US008711167B2

(12) United States Patent
Wyatt

(10) Patent No.: US 8,711,167 B2
(45) Date of Patent: Apr. 29, 2014

(54) METHOD AND APPARATUS FOR GENERATING IMAGES USING A COLOR FIELD SEQUENTIAL DISPLAY

(75) Inventor: David Wyatt, San Jose, CA (US)

(73) Assignee: Nvidia Corporation, Santa Clara, CA (US)

( * ) Notice: Subject to any disclaimer, the term of this patent is extended or adjusted under 35 U.S.C. 154(b) by 369 days.

(21) Appl. No.: 13/104,867

(22) Filed: May 10, 2011

(65) Prior Publication Data

US 2012/0287139 A1 Nov. 15, 2012

(51) Int. Cl.

| | |
|---|---|
| ***G09G 5/02*** | (2006.01) |
| ***G09G 3/28*** | (2013.01) |
| ***G09G 3/36*** | (2006.01) |
| ***A61B 1/06*** | (2006.01) |
| ***H04N 9/04*** | (2006.01) |
| ***H04N 9/64*** | (2006.01) |
| ***G06K 9/00*** | (2006.01) |
| ***G06K 9/40*** | (2006.01) |
| ***G06K 9/60*** | (2006.01) |

(52) U.S. Cl.

USPC ........... 345/589; 345/600; 345/549; 345/592; 345/63; 345/102; 348/70; 348/715; 348/269; 382/167; 382/274; 382/305; 359/26

(58) Field of Classification Search

CPC ............. G09G 5/02; G09G 5/36; G09G 3/28; G09G 3/38; G09G 5/06; G09G 3/3406; G09G 3/2022; G06F 13/14; G06F 17/30265; H04N 2005/2255; H04N 9/045; H04N 5/907; G06T 5/001; G06T 5/40

USPC ............. 345/84, 87, 109, 581, 589, 600–601, 345/591–592, 606, 545–549, 204, 690–691, 345/694, 22, 36, 56, 63, 76–77, 89, 102; 348/40–42, 70–71, 251–256, 268–269, 348/427–430, 435, 439, 455–456, 459, 478, 348/513–514, 536–539, 552, 557, 711, 348/714–715; 359/26, 227–228, 230, 237, 359/251, 253, 255, 283, 290, 389; 382/162, 382/167, 254, 274, 276, 305

See application file for complete search history.

(56) References Cited

U.S. PATENT DOCUMENTS

| | | | | |
|---|---|---|---|---|
| 6,707,516 | B1 * | 3/2004 | Johnson et al. | 349/78 |
| 6,831,621 | B2 * | 12/2004 | Nakano | 345/87 |

(Continued)

OTHER PUBLICATIONS

PCT Search Report, PCT/US2012/037385 dated Jul. 16, 2012.

(Continued)

*Primary Examiner* — Wesner Sajous

(74) *Attorney, Agent, or Firm* — Patterson + Sheridan, L.L.P.

(57) ABSTRACT

One embodiment of the present invention sets forth a technique for generating and transmitting video frame data from a graphics processing unit (GPU) to a color field sequential display device. A frame buffer image comprising per-pixel packed color channels is transformed to a frame buffer image comprising regions corresponding to the color channels with vertical blanking regions inserted between color sub-field regions. Each region of the transformed frame buffer image is sequentially transmitted to the color field sequential display device for display of the corresponding color channel. Backlight illumination for each color channel is controlled by the GPU for temporal alignment with display of each color channel during a vertical blanking interval. The GPU may compensate an individual pixel's color channel value based on a corresponding previous color channel value in order to minimize crosstalk between neighboring color fields.

25 Claims, 18 Drawing Sheets

(56) References Cited

U.S. PATENT DOCUMENTS

| | | | | |
|---|---|---|---|---|
| 7,190,518 | B1 * | 3/2007 | Kleinberger et al. | 359/465 |
| 2003/0117355 | A1 * | 6/2003 | Yamauchi | 345/87 |
| 2003/0122828 | A1 * | 7/2003 | Lukyanitsa | 345/440 |
| 2003/0231191 | A1 * | 12/2003 | Glen | 345/690 |
| 2006/0146007 | A1 * | 7/2006 | Lim et al. | 345/102 |
| 2007/0035493 | A1 * | 2/2007 | Chang | 345/87 |
| 2009/0140965 | A1 * | 6/2009 | Ishiguchi et al. | 345/87 |
| 2009/0160757 | A1 * | 6/2009 | Robinson | 345/102 |
| 2010/0097449 | A1 | 4/2010 | Jeong et al. | |
| 2010/0295866 | A1 * | 11/2010 | Ishii | 345/597 |
| 2011/0063330 | A1 * | 3/2011 | Bae et al. | 345/690 |
| 2011/0102445 | A1 | 5/2011 | Harada et al. | |
| 2011/0298840 | A1 * | 12/2011 | Chen | 345/690 |

OTHER PUBLICATIONS

Non-Final Office Action dated Jun. 17, 2013, U.S. Appl. No. 13/104,876, filed May 10, 2011, 15 pages.

* cited by examiner

METHOD AND APPARATUS FOR GENERATING IMAGES USING A COLOR FIELD SEQUENTIAL DISPLAY

BACKGROUND OF THE INVENTION

1. Field of the Invention

Embodiments of the invention relate generally to, and more specifically to a method and apparatus for generating images using a color field sequential display.

2. Description of the Related Art

A color field sequential (CFS) display comprises a two-dimensional array of pixels that are illuminated with a sequence of backlight colors corresponding to pixel color channels. The backlight colors for each pixel are combined into a single perceived color via temporal integration, a fundamental characteristic of human visual perception. A CFS display based on liquid crystal display (LCD) technology comprises a two-dimensional array of gray scale pixels and a backlight configured to cycle through a sequence of primary colors, such as red, green and blue, corresponding to the color channels within each pixel of the image to be displayed. As the LCD backlight is cycled through each color, the gray scale pixels are configured to emit an intensity of light for the corresponding color. While each gray scale pixel only emits a single color at a time, temporal integration yields a complete color when observed by a viewer.

Conventional LCD devices are configured to receive packed red, green, and blue pixel data because the packed pixel data is required, on a line-by-line basis, for proper refresh of the conventional LCD device. Similarly, conventional graphics devices are configured to generate packed pixel data for display. However, because only one color channel is actually displayed at a time in a CFS display device, the CFS display device needs to store data for the other color channels not currently being displayed. For example, a CFS display device may receive packed red, green, and blue data, but may only display data for one color channel for the duration of a given display frame. Initially, only red data is displayed, followed by only green data, followed by only blue data. In order to be available for subsequent display, the green and blue data needs to be stored within the CFS display device. However, storing complete frames of data adds cost and complexity to the CFS display device.

As the foregoing illustrates, what is needed in the art is a technique for eliminating frame storage within the CFS display device.

SUMMARY OF THE INVENTION

One embodiment of the invention sets forth a method for displaying color frame information on a color field sequential display. The method includes reading pixel data from an input frame buffer that is organized as packed color channels, where a separate color channel exists for each color in the color field of the sequential display, extracting color channel information from the pixel data for each color channel, generating frame buffer write data from the color channel information, and storing the frame buffer write data as color sub-frame information in a target frame buffer.

One advantage of the techniques described herein is that a new pixel value for display may be modified to compensate for a difference between the new pixel value and a previous pixel value. The difference can lead to inter-frame noise interference that degrades image quality. Compensating the new pixel value reduces inter-frame noise. Furthermore, an auto-stereoscopic display based on the color field sequential display device is advantageous versus the prior art because chromatic fringing associated with conventional RGB display technology is eliminated in the color field sequential display device.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

System Overview

Figure 1:
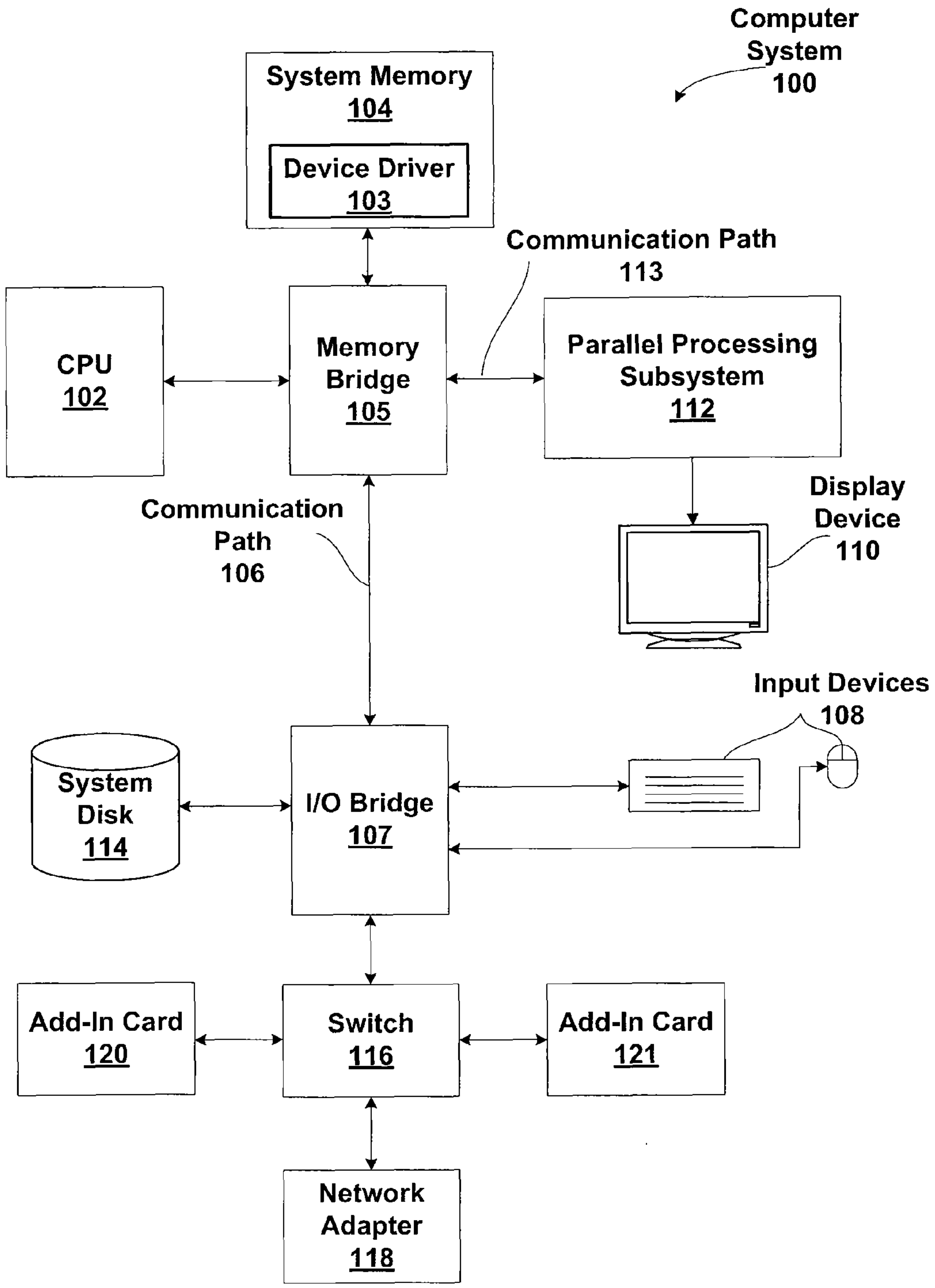
FIG. 1 is a block diagram illustrating a computer system configured to implement one or more aspects of the present invention.

FIG. 1 is a block diagram illustrating a computer system 100 configured to implement one or more aspects of the present invention. Computer system 100 includes a central processing unit (CPU) 102 and a system memory 104 communicating via an interconnection path that may include a memory bridge 105. Memory bridge 105, which may be, e.g., a Northbridge chip, is connected via a bus or other communication path 106 (e.g., a HyperTransport link) to an I/O (input/output) bridge 107. I/O bridge 107, which may be, e.g., a Southbridge chip, receives user input from one or more user input devices 108 (e.g., keyboard, mouse) and forwards the input to CPU 102 via path 106 and memory bridge 105. A parallel processing subsystem 112 is coupled to memory bridge 105 via a bus or other communication path 113 (e.g., a PCI Express, Accelerated Graphics Port, or HyperTransport link); in one embodiment parallel processing subsystem 112 is a graphics subsystem that delivers pixels to a display device 110 (e.g., a conventional CRT or LCD based monitor). A system disk 114 is also connected to I/O bridge 107. A switch 116 provides connections between I/O bridge 107 and other components such as a network adapter 118 and various add-in cards 120 and 121. Other components (not explicitly shown), including USB or other port connections, CD drives, DVD drives, film recording devices, and the like, may also be connected to I/O bridge 107. Communication paths interconnecting the various components in FIG. 1 may be implemented using any suitable protocols, such as PCI (Peripheral Component Interconnect), PCI-Express, AGP (Accelerated Graphics Port), HyperTransport, or any other bus or point-to-point communication protocol(s), and connections between different devices may use different protocols as is known in the art.

In one embodiment, the parallel processing subsystem 112 incorporates circuitry optimized for graphics and video processing, including, for example, video output circuitry, and constitutes a graphics processing unit (GPU). In another embodiment, the parallel processing subsystem 112 incorporates circuitry optimized for general purpose processing, while preserving the underlying computational architecture, described in greater detail herein. In yet another embodiment, the parallel processing subsystem 112 may be integrated with one or more other system elements, such as the memory bridge 105, CPU 102, and I/O bridge 107 to form a system on chip (SoC).

It will be appreciated that the system shown herein is illustrative and that variations and modifications are possible. The connection topology, including the number and arrangement of bridges, the number of CPUs 102, and the number of parallel processing subsystems 112, may be modified as desired. For instance, in some embodiments, system memory 104 is connected to CPU 102 directly rather than through a bridge, and other devices communicate with system memory 104 via memory bridge 105 and CPU 102. In other alternative topologies, parallel processing subsystem 112 is connected to I/O bridge 107 or directly to CPU 102, rather than to memory bridge 105. In still other embodiments, I/O bridge 107 and memory bridge 105 might be integrated into a single chip. Large embodiments may include two or more CPUs 102 and two or more parallel processing systems 112. The particular components shown herein are optional; for instance, any number of add-in cards or peripheral devices might be supported. In some embodiments, switch 116 is eliminated, and network adapter 118 and add-in cards 120, 121 connect directly to I/O bridge 107.

Figure 2:
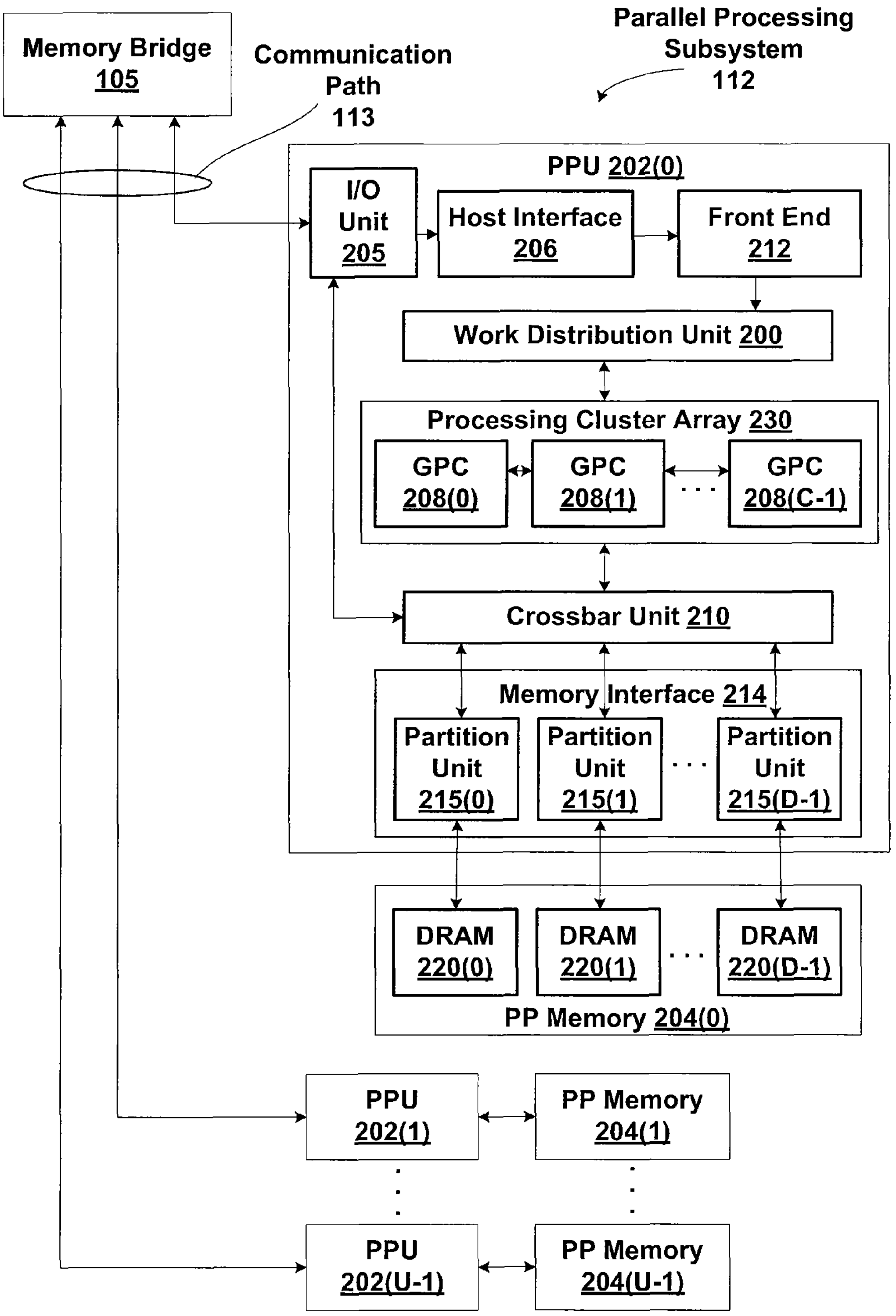
FIG. 2 is a block diagram of a parallel processing subsystem for the computer system of FIG. 1, according to one embodiment of the present invention.

FIG. 2 illustrates a parallel processing subsystem 112, according to one embodiment of the present invention. As shown, parallel processing subsystem 112 includes one or more parallel processing units (PPUs) 202, each of which is coupled to a local parallel processing (PP) memory 204. In general, a parallel processing subsystem includes a number U of PPUs, where U≥1. (Herein, multiple instances of like objects are denoted with reference numbers identifying the object and parenthetical numbers identifying the instance where needed.) PPUs 202 and parallel processing memories 204 may be implemented using one or more integrated circuit devices, such as programmable processors, application specific integrated circuits (ASICs), or memory devices, or in any other technically feasible fashion.

Referring again to FIG. 1, in some embodiments, some or all of PPUs 202 in parallel processing subsystem 112 are graphics processors with rendering pipelines that can be configured to perform various tasks related to generating pixel data from graphics data supplied by CPU 102 and/or system memory 104 via memory bridge 105 and bus 113, interacting with local parallel processing memory 204 (which can be used as graphics memory including, e.g., a conventional frame buffer) to store and update pixel data, delivering pixel data to display device 110, and the like. In some embodiments, parallel processing subsystem 112 may include one or more PPUs 202 that operate as graphics processors and one or more other PPUs 202 that are used for general-purpose computations. The PPUs may be identical or different, and each PPU may have its own dedicated parallel processing memory device(s) or no dedicated parallel processing memory device (s). One or more PPUs 202 may output data to display device 110 or each PPU 202 may output data to one or more display devices 110.

In operation, CPU 102 is the master processor of computer system 100, controlling and coordinating operations of other system components. In particular, CPU 102 issues commands that control the operation of PPUs 202. In some embodiments, CPU 102 writes a stream of commands for each PPU 202 to a pushbuffer (not explicitly shown in either FIG. 1 or FIG. 2) that may be located in system memory 104, parallel processing memory 204, or another storage location accessible to both CPU 102 and PPU 202. PPU 202 reads the command stream from the pushbuffer and then executes commands asynchronously relative to the operation of CPU 102.

Referring back now to FIG. 2, each PPU 202 includes an I/O (input/output) unit 205 that communicates with the rest of computer system 100 via communication path 113, which connects to memory bridge 105 (or, in one alternative embodiment, directly to CPU 102). The connection of PPU 202 to the rest of computer system 100 may also be varied. In some embodiments, parallel processing subsystem 112 is implemented as an add-in card that can be inserted into an expansion slot of computer system 100. In other embodiments, a PPU 202 can be integrated on a single chip with a bus bridge, such as memory bridge 105 or I/O bridge 107. In still other embodiments, some or all elements of PPU 202 may be integrated on a single chip with CPU 102.

In one embodiment, communication path 113 is a PCI-EXPRESS link, in which dedicated lanes are allocated to each PPU 202, as is known in the art. Other communication paths may also be used. An I/O unit 205 generates packets (or other signals) for transmission on communication path 113 and also receives all incoming packets (or other signals) from communication path 113, directing the incoming packets to appropriate components of PPU 202. For example, commands related to processing tasks may be directed to a host interface 206, while commands related to memory operations (e.g., reading from or writing to parallel processing memory 204) may be directed to a memory crossbar unit 210. Host interface 206 reads each pushbuffer and outputs the work specified by the pushbuffer to a front end 212.

Each PPU 202 advantageously implements a highly parallel processing architecture. As shown in detail, PPU 202(0) includes a processing cluster array 230 that includes a number C of general processing clusters (GPCs) 208, where C≥1. Each GPC 208 is capable of executing a large number (e.g., hundreds or thousands) of threads concurrently, where each thread is an instance of a program. In various applications, different GPCs 208 may be allocated for processing different types of programs or for performing different types of computations. For example, in a graphics application, a first set of GPCs 208 may be allocated to perform tessellation operations and to produce primitive topologies for patches, and a second set of GPCs 208 may be allocated to perform tessellation shading to evaluate patch parameters for the primitive topologies and to determine vertex positions and other per-vertex attributes. The allocation of GPCs 208 may vary dependent on the workload arising for each type of program or computation.

GPCs 208 receive processing tasks to be executed via a work distribution unit 200, which receives commands defining processing tasks from front end unit 212. Processing tasks include indices of data to be processed, e.g., surface (patch) data, primitive data, vertex data, and/or pixel data, as well as state parameters and commands defining how the data is to be processed (e.g., what program is to be executed). Work distribution unit 200 may be configured to fetch the indices corresponding to the tasks, or work distribution unit 200 may receive the indices from front end 212. Front end 212 ensures that GPCs 208 are configured to a valid state before the processing specified by the pushbuffers is initiated.

When PPU 202 is used for graphics processing, for example, the processing workload for each patch is divided into approximately equal sized tasks to enable distribution of the tessellation processing to multiple GPCs 208. A work distribution unit 200 may be configured to produce tasks at a frequency capable of providing tasks to multiple GPCs 208 for processing. By contrast, in conventional systems, processing is typically performed by a single processing engine, while the other processing engines remain idle, waiting for the single processing engine to complete its tasks before beginning their processing tasks. In some embodiments of the present invention, portions of GPCs 208 are configured to perform different types of processing. For example a first portion may be configured to perform vertex shading and topology generation, a second portion may be configured to perform tessellation and geometry shading, and a third portion may be configured to perform pixel shading in screen space to produce a rendered image. Intermediate data produced by GPCs 208 may be stored in buffers to allow the intermediate data to be transmitted between GPCs 208 for further processing.

Memory interface 214 includes a number D of partition units 215 that are each directly coupled to a portion of parallel processing memory 204, where D≥1. As shown, the number of partition units 215 generally equals the number of DRAM 220. In other embodiments, the number of partition units 215 may not equal the number of memory devices. Persons skilled in the art will appreciate that DRAM 220 may be replaced with other suitable storage devices and can be of generally conventional design. A detailed description is therefore omitted. Render targets, such as frame buffers or texture maps may be stored across DRAMs 220, allowing partition units 215 to write portions of each render target in parallel to efficiently use the available bandwidth of parallel processing memory 204.

Any one of GPCs 208 may process data to be written to any of the DRAMs 220 within parallel processing memory 204. Crossbar unit 210 is configured to route the output of each GPC 208 to the input of any partition unit 215 or to another GPC 208 for further processing. GPCs 208 communicate with memory interface 214 through crossbar unit 210 to read from or write to various external memory devices. In one embodiment, crossbar unit 210 has a connection to memory interface 214 to communicate with I/O unit 205, as well as a connection to local parallel processing memory 204, thereby enabling the processing cores within the different GPCs 208 to communicate with system memory 104 or other memory that is not local to PPU 202. In the embodiment shown in FIG. 2, crossbar unit 210 is directly connected with I/O unit 205. Crossbar unit 210 may use virtual channels to separate traffic streams between the GPCs 208 and partition units 215.

Again, GPCs 208 can be programmed to execute processing tasks relating to a wide variety of applications, including but not limited to, linear and nonlinear data transforms, filtering of video and/or audio data, modeling operations (e.g., applying laws of physics to determine position, velocity and other attributes of objects), image rendering operations (e.g., tessellation shader, vertex shader, geometry shader, and/or pixel shader programs), and so on. PPUs 202 may transfer data from system memory 104 and/or local parallel processing memories 204 into internal (on-chip) memory, process the data, and write result data back to system memory 104 and/or local parallel processing memories 204, where such data can be accessed by other system components, including CPU 102 or another parallel processing subsystem 112.

A PPU 202 may be provided with any amount of local parallel processing memory 204, including no local memory, and may use local memory and system memory in any combination. For instance, a PPU 202 can be a graphics processor in a unified memory architecture (UMA) embodiment. In such embodiments, little or no dedicated graphics (parallel processing) memory would be provided, and PPU 202 would use system memory exclusively or almost exclusively. In UMA embodiments, a PPU 202 may be integrated into a bridge chip or processor chip or provided as a discrete chip with a high-speed link (e.g., PCI-EXPRESS) connecting the PPU 202 to system memory via a bridge chip or other communication means.

As noted above, any number of PPUs 202 can be included in a parallel processing subsystem 112. For instance, multiple PPUs 202 can be provided on a single add-in card, or multiple add-in cards can be connected to communication path 113, or one or more of PPUs 202 can be integrated into a bridge chip. PPUs 202 in a multi-PPU system may be identical to or different from one another. For instance, different PPUs 202 might have different numbers of processing cores, different amounts of local parallel processing memory, and so on. Where multiple PPUs 202 are present, those PPUs may be operated in parallel to process data at a higher throughput than is possible with a single PPU 202. Systems incorporating one or more PPUs 202 may be implemented in a variety of configurations and form factors, including desktop, laptop, or handheld personal computers, servers, workstations, game consoles, embedded systems, and the like.

Processing Cluster Array Overview

Figure 3A:
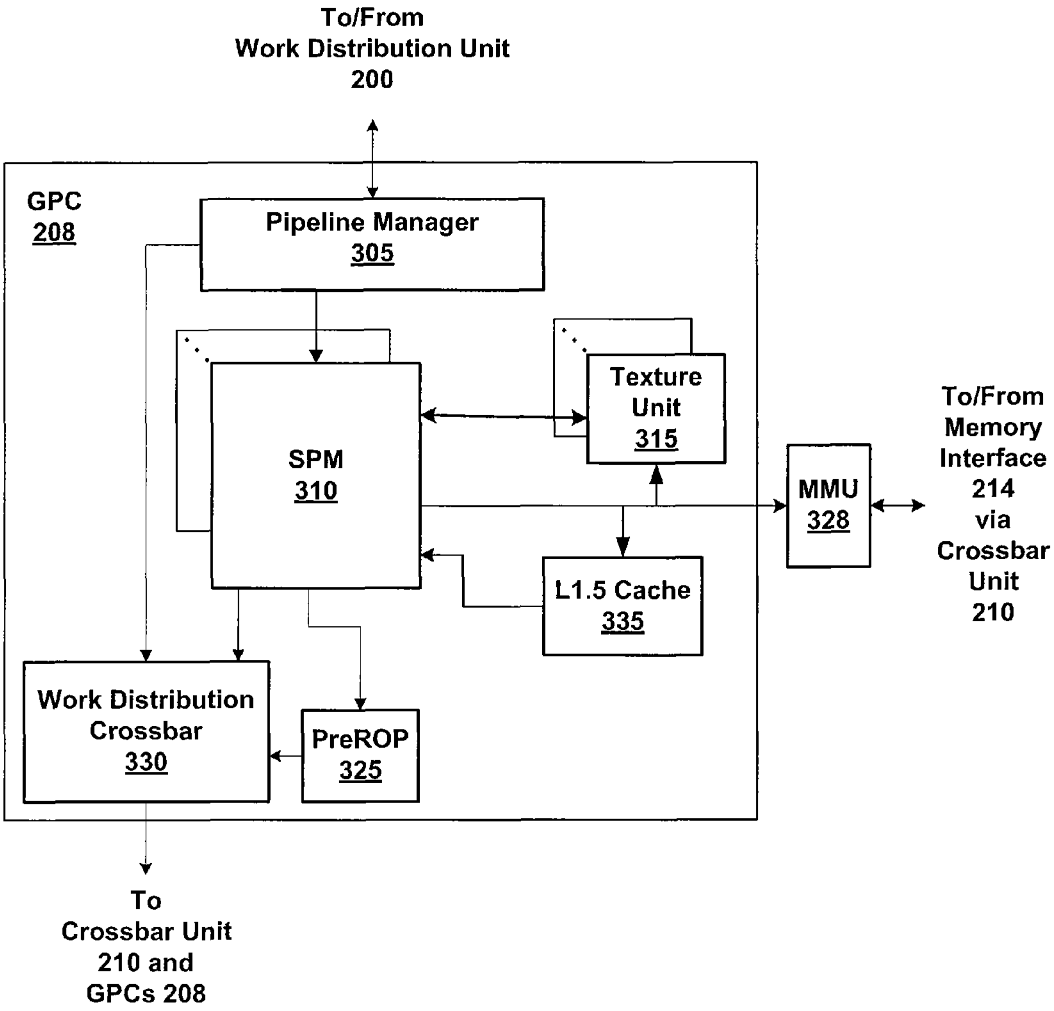
FIG. 3A is a block diagram of a GPC within one of the PPUs of FIG. 2, according to one embodiment of the present invention.

FIG. 3A is a block diagram of a GPC 208 within one of the PPUs 202 of FIG. 2, according to one embodiment of the present invention. Each GPC 208 may be configured to execute a large number of threads in parallel, where the term "thread" refers to an instance of a particular program executing on a particular set of input data. In some embodiments, single-instruction, multiple-data (SIMD) instruction issue techniques are used to support parallel execution of a large number of threads without providing multiple independent instruction units. In other embodiments, single-instruction, multiple-thread (SIMT) techniques are used to support parallel execution of a large number of generally synchronized threads, using a common instruction unit configured to issue instructions to a set of processing engines within each one of the GPCs 208. Unlike a SIMD execution regime, where all processing engines typically execute identical instructions, SIMT execution allows different threads to more readily follow divergent execution paths through a given thread program. Persons skilled in the art will understand that a SIMD processing regime represents a functional subset of a SIMT processing regime.

Operation of GPC 208 is advantageously controlled via a pipeline manager 305 that distributes processing tasks to streaming multiprocessors (SPMs) 310. Pipeline manager 305 may also be configured to control a work distribution crossbar 330 by specifying destinations for processed data output by SPMs 310.

In one embodiment, each GPC 208 includes a number M of SPMs 310, where M≥1, each SPM 310 configured to process one or more thread groups. Also, each SPM 310 advantageously includes an identical set of functional execution units (e.g., arithmetic logic units, and load-store units, shown as Exec units 302 and LSUs 303 in FIG. 3C) that may be pipelined, allowing a new instruction to be issued before a previous instruction has finished, as is known in the art. Any combination of functional execution units may be provided. In one embodiment, the functional units support a variety of operations including integer and floating point arithmetic (e.g., addition and multiplication), comparison operations, Boolean operations (AND, OR, XOR), bit-shifting, and computation of various algebraic functions (e.g., planar interpolation, trigonometric, exponential, and logarithmic functions, etc.); and the same functional-unit hardware can be leveraged to perform different operations.

The series of instructions transmitted to a particular GPC 208 constitutes a thread, as previously defined herein, and the collection of a certain number of concurrently executing threads across the parallel processing engines (not shown) within an SPM 310 is referred to herein as a "warp" or "thread group." As used herein, a "thread group" refers to a group of threads concurrently executing the same program on different input data, with one thread of the group being assigned to a different processing engine within an SPM 310. A thread group may include fewer threads than the number of processing engines within the SPM 310, in which case some processing engines will be idle during cycles when that thread group is being processed. A thread group may also include more threads than the number of processing engines within the SPM 310, in which case processing will take place over consecutive clock cycles. Since each SPM 310 can support up to G thread groups concurrently, it follows that up to G*M thread groups can be executing in GPC 208 at any given time.

Additionally, a plurality of related thread groups may be active (in different phases of execution) at the same time within an SPM 310. This collection of thread groups is referred to herein as a "cooperative thread array" ("CTA") or "thread array." The size of a particular CTA is equal to m*k, where k is the number of concurrently executing threads in a thread group and is typically an integer multiple of the number of parallel processing engines within the SPM 310, and m is the number of thread groups simultaneously active within the SPM 310. The size of a CTA is generally determined by the programmer and the amount of hardware resources, such as memory or registers, available to the CTA.

Each SPM 310 contains an L1 cache (not shown) or uses space in a corresponding L1 cache outside of the SPM 310 that is used to perform load and store operations. Each SPM 310 also has access to L2 caches within the partition units 215 that are shared among all GPCs 208 and may be used to transfer data between threads. Finally, SPMs 310 also have access to off-chip "global" memory, which can include, e.g., parallel processing memory 204 and/or system memory 104. It is to be understood that any memory external to PPU 202 may be used as global memory. Additionally, an L1.5 cache 335 may be included within the GPC 208, configured to receive and hold data fetched from memory via memory interface 214 requested by SPM 310, including instructions, uniform data, and constant data, and provide the requested data to SPM 310. Embodiments having multiple SPMs 310 in GPC 208 beneficially share common instructions and data cached in L1.5 cache 335.

Each GPC 208 may include a memory management unit (MMU) 328 that is configured to map virtual addresses into physical addresses. In other embodiments, MMU(s) 328 may reside within the memory interface 214. The MMU 328 includes a set of page table entries (PTEs) used to map a virtual address to a physical address of a tile and optionally a cache line index. The MMU 328 may include address translation lookaside buffers (TLB) or caches which may reside within multiprocessor SPM 310 or the L1 cache or GPC 208. The physical address is processed to distribute surface data access locality to allow efficient request interleaving among partition units. The cache line index may be used to determine whether of not a request for a cache line is a hit or miss.

In graphics and computing applications, a GPC 208 may be configured such that each SPM 310 is coupled to a texture unit 315 for performing texture mapping operations, e.g., determining texture sample positions, reading texture data, and filtering the texture data. Texture data is read from an internal texture L1 cache (not shown) or in some embodiments from the L1 cache within SPM 310 and is fetched from an L2 cache, parallel processing memory 204, or system memory 104, as needed. Each SPM 310 outputs processed tasks to work distribution crossbar 330 in order to provide the processed task to another GPC 208 for further processing or to store the processed task in an L2 cache, parallel processing memory 204, or system memory 104 via crossbar unit 210. A preROP (pre-raster operations) 325 is configured to receive data from SPM 310, direct data to ROP units within partition units 215, and perform optimizations for color blending, organize pixel color data, and perform address translations.

It will be appreciated that the core architecture described herein is illustrative and that variations and modifications are possible. Any number of processing units, e.g., SPMs 310 or texture units 315, preROPs 325 may be included within a GPC 208. Further, while only one GPC 208 is shown, a PPU 202 may include any number of GPCs 208 that are advantageously functionally similar to one another so that execution behavior does not depend on which GPC 208 receives a particular processing task. Further, each GPC 208 advantageously operates independently of other GPCs 208 using separate and distinct processing units, L1 caches, and so on.

Figure 3B:
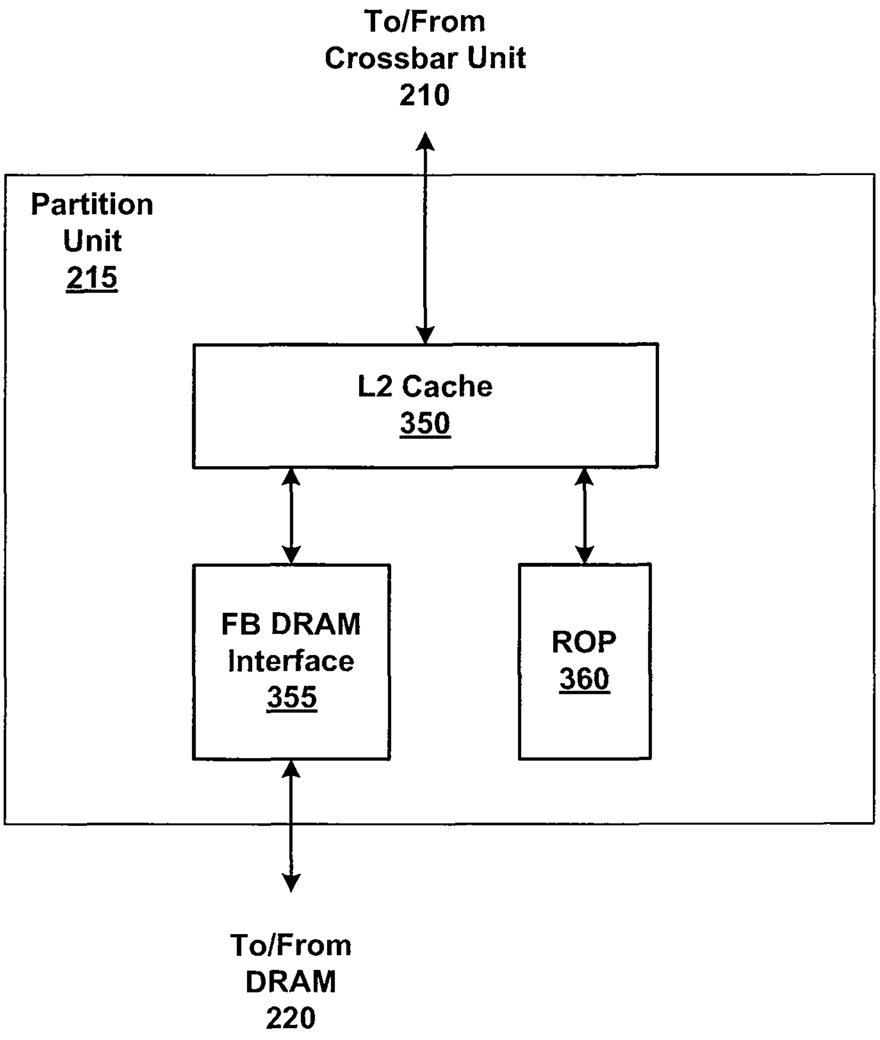
FIG. 3B is a block diagram of a partition unit within one of the PPUs of FIG. 2, according to one embodiment of the present invention.

FIG. 3B is a block diagram of a partition unit 215 within one of the PPUs 202 of FIG. 2, according to one embodiment of the present invention. As shown, partition unit 215 includes a L2 cache 350, a frame buffer (FB) DRAM interface 355, and a raster operations unit (ROP) 360. L2 cache 350 is a read/write cache that is configured to perform load and store operations received from crossbar unit 210 and ROP 360. Read misses and urgent writeback requests are output by L2 cache 350 to FB DRAM interface 355 for processing. Dirty updates are also sent to FB 355 for opportunistic processing. FB 355 interfaces directly with DRAM 220, outputting read and write requests and receiving data read from DRAM 220.

In graphics applications, ROP 360 is a processing unit that performs raster operations, such as stencil, z test, blending, and the like, and outputs pixel data as processed graphics data for storage in graphics memory. In some embodiments of the present invention, ROP 360 is included within each GPC 208 instead of partition unit 215, and pixel read and write requests are transmitted over crossbar unit 210 instead of pixel fragment data.

The processed graphics data may be displayed on display device 110 or routed for further processing by CPU 102 or by one of the processing entities within parallel processing subsystem 112. Each partition unit 215 includes a ROP 360 in order to distribute processing of the raster operations. In some embodiments, ROP 360 may be configured to compress z or color data that is written to memory and decompress z or color data that is read from memory.

Persons skilled in the art will understand that the architecture described in FIGS. 1, 2, 3A, and 3B in no way limits the scope of the present invention and that the techniques taught herein may be implemented on any properly configured processing unit, including, without limitation, one or more CPUs, one or more multi-core CPUs, one or more PPUs 202, one or more GPCs 208, one or more graphics or special purpose processing units, or the like, without departing the scope of the present invention.

In embodiments of the present invention, it is desirable to use PPU 122 or other processor(s) of a computing system to execute general-purpose computations using thread arrays. Each thread in the thread array is assigned a unique thread identifier ("thread ID") that is accessible to the thread during its execution. The thread ID, which can be defined as a one-dimensional or multi-dimensional numerical value controls various aspects of the thread's processing behavior. For instance, a thread ID may be used to determine which portion of the input data set a thread is to process and/or to determine which portion of an output data set a thread is to produce or write.

A sequence of per-thread instructions may include at least one instruction that defines a cooperative behavior between the representative thread and one or more other threads of the thread array. For example, the sequence of per-thread instructions might include an instruction to suspend execution of operations for the representative thread at a particular point in the sequence until such time as one or more of the other threads reach that particular point, an instruction for the representative thread to store data in a shared memory to which one or more of the other threads have access, an instruction for the representative thread to atomically read and update data stored in a shared memory to which one or more of the other threads have access based on their thread IDs, or the like. The CTA program can also include an instruction to compute an address in the shared memory from which data is to be read, with the address being a function of thread ID. By defining suitable functions and providing synchronization techniques, data can be written to a given location in shared memory by one thread of a CTA and read from that location by a different thread of the same CTA in a predictable manner. Consequently, any desired pattern of data sharing among threads can be supported, and any thread in a CTA can share data with any other thread in the same CTA. The extent, if any, of data sharing among threads of a CTA is determined by the CTA program; thus, it is to be understood that in a particular application that uses CTAs, the threads of a CTA might or might not actually share data with each other, depending on the CTA program, and the terms "CIA" and "thread array" are used synonymously herein.

Figure 3C:
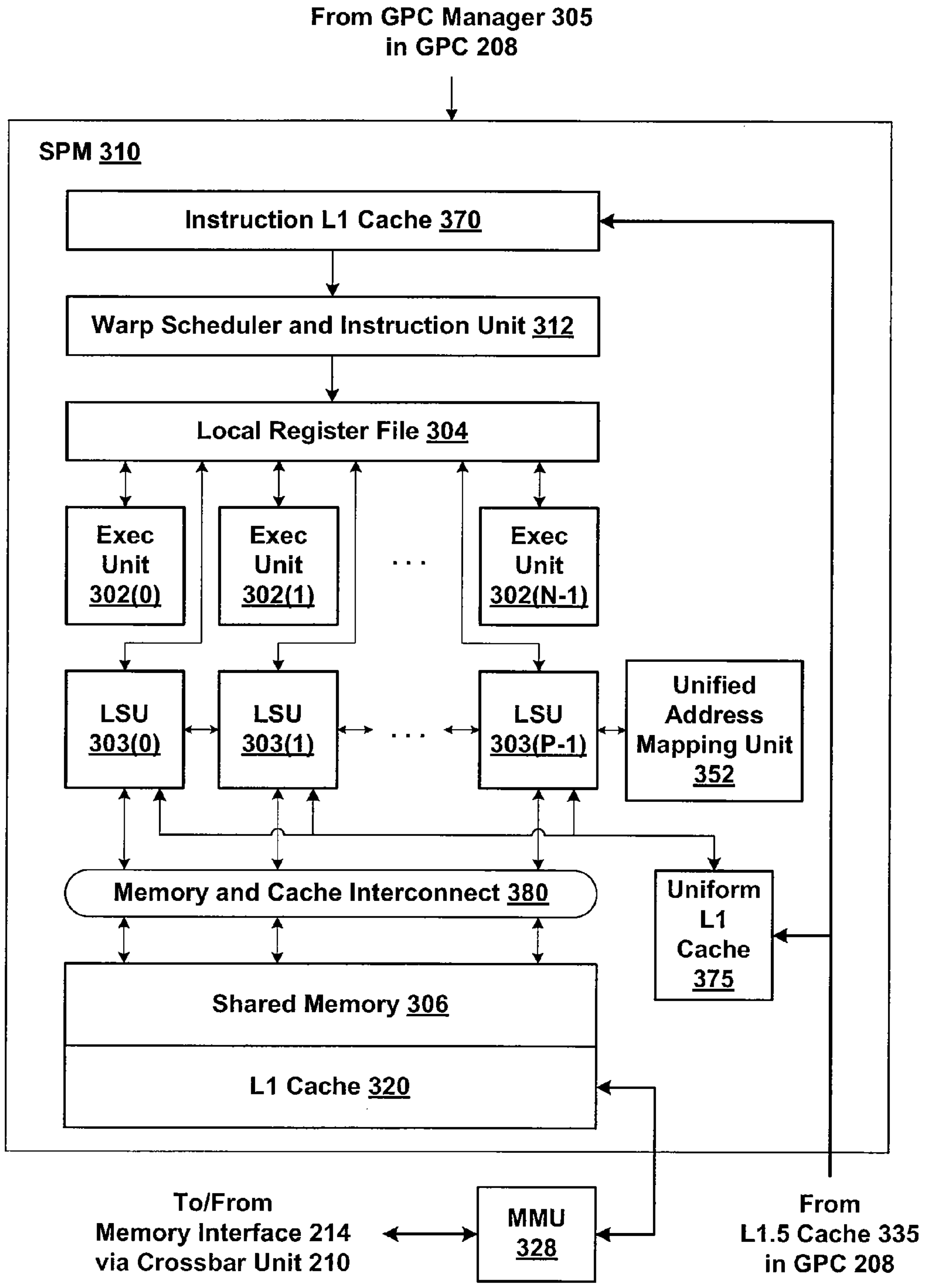
FIG. 3C is a block diagram of a portion of the SPM of FIG. 3A, according to one embodiment of the present invention.

FIG. 3C is a block diagram of the SPM 310 of FIG. 3A, according to one embodiment of the present invention. The SPM 310 includes an instruction L1 cache 370 that is configured to receive instructions and constants from memory via L1.5 cache 335. A warp scheduler and instruction unit 312 receives instructions and constants from the instruction L1 cache 370 and controls local register file 304 and SPM 310 functional units according to the instructions and constants. The SPM 310 functional units include N exec (execution or processing) units 302 and P load-store units (LSU) 303.

SPM 310 provides on-chip (internal) data storage with different levels of accessibility. Special registers (not shown) are readable but not writeable by LSU 303 and are used to store parameters defining each CTA thread's "position." In one embodiment, special registers include one register per CTA thread (or per exec unit 302 within SPM 310) that stores a thread ID; each thread ID register is accessible only by a respective one of the exec unit 302. Special registers may also include additional registers, readable by all CTA threads (or by all LSUs 303) that store a CTA identifier, the CTA dimensions, the dimensions of a grid to which the CTA belongs, and an identifier of a grid to which the CTA belongs. Special registers are written during initialization in response to commands received via front end 212 from device driver 103 and do not change during CTA execution.

A parameter memory (not shown) stores runtime parameters (constants) that can be read but not written by any CTA thread (or any LSU 303). In one embodiment, device driver 103 provides parameters to the parameter memory before directing SPM 310 to begin execution of a CTA that uses these parameters. Any CTA thread within any CTA (or any exec unit 302 within SPM 310) can access global memory through a memory interface 214. Portions of global memory may be stored in the L1 cache 320.

Local register file 304 is used by each CTA thread as scratch space; each register is allocated for the exclusive use of one thread, and data in any of local register file 304 is accessible only to the CTA thread to which it is allocated. Local register file 304 can be implemented as a register file that is physically or logically divided into P lanes, each having some number of entries (where each entry might store, e.g., a 32-bit word). One lane is assigned to each of the N exec units 302 and P load-store units LSU 303, and corresponding entries in different lanes can be populated with data for different threads executing the same program to facilitate SIMD execution. Different portions of the lanes can be allocated to different ones of the G concurrent thread groups, so that a given entry in the local register file 304 is accessible only to a particular thread. In one embodiment, certain entries within the local register file 304 are reserved for storing thread identifiers, implementing one of the special registers.

Shared memory 306 is accessible to all CTA threads (within a single CTA); any location in shared memory 306 is accessible to any CTA thread within the same CTA (or to any processing engine within SPM 310). Shared memory 306 can be implemented as a shared register file or shared on-chip cache memory with an interconnect that allows any processing engine to read from or write to any location in the shared memory. In other embodiments, shared state space might map onto a per-CIA region of off-chip memory, and be cached in L1 cache 320. The parameter memory can be implemented as a designated section within the same shared register file or shared cache memory that implements shared memory 306, or as a separate shared register file or on-chip cache memory to which the LSUs 303 have read-only access. In one embodiment, the area that implements the parameter memory is also used to store the CTA ID and grid ID, as well as CTA and grid dimensions, implementing portions of the special registers. Each LSU 303 in SPM 310 is coupled to a unified address mapping unit 352 that converts an address provided for load and store instructions that are specified in a unified memory space into an address in each distinct memory space. Consequently, an instruction may be used to access any of the local, shared, or global memory spaces by specifying an address in the unified memory space.

The L1 Cache 320 in each SPM 310 can be used to cache private per-thread local data and also per-application global data. In some embodiments, the per-CTA shared data may be cached in the L1 cache 320. The LSUs 303 are coupled to a uniform L1 cache 371, the shared memory 306, and the L1 cache 320 via a memory and cache interconnect 380. The uniform L1 cache 371 is configured to receive read-only data and constants from memory via the L1.5 Cache 335.

Figure 4:
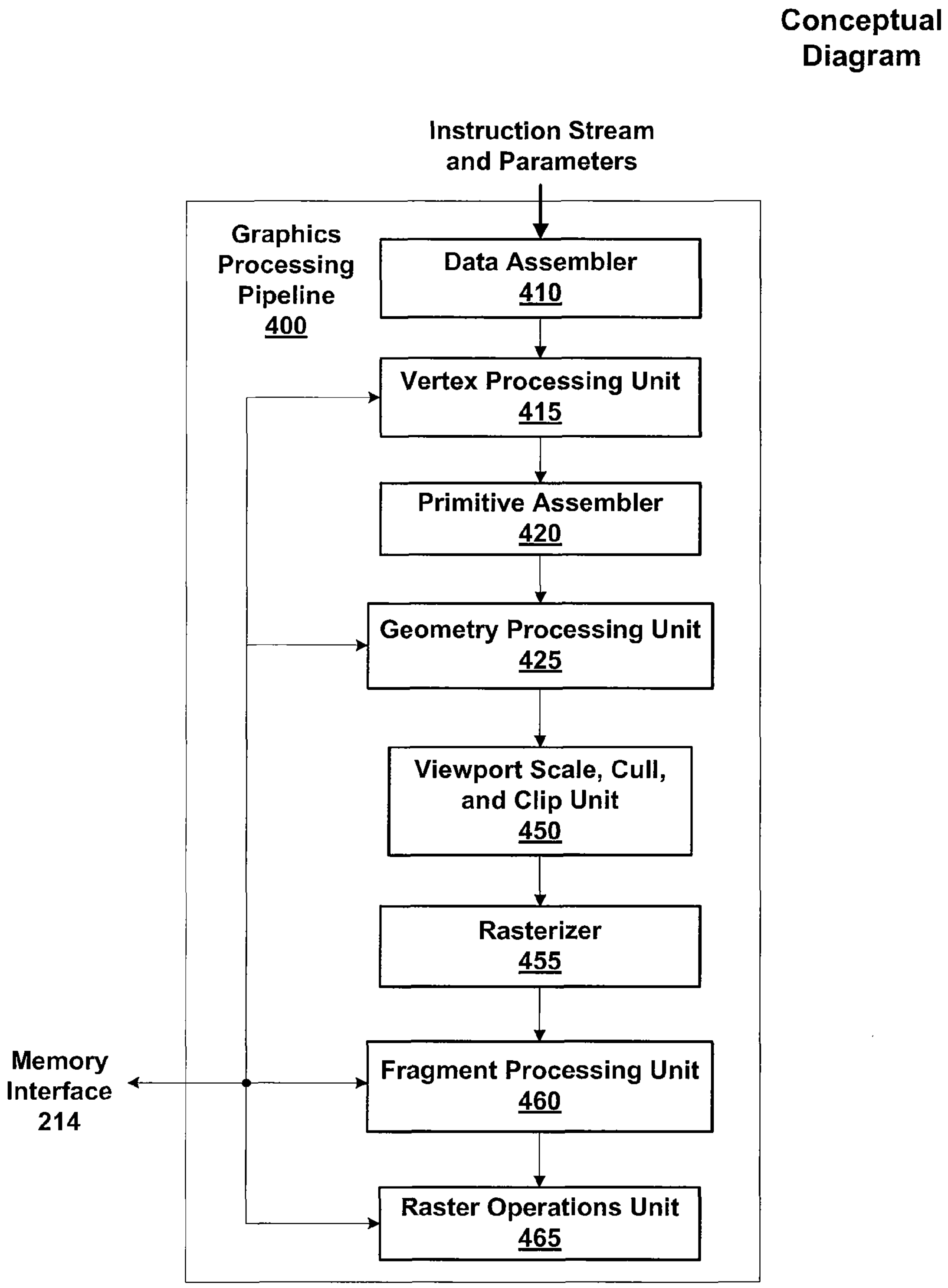
FIG. 4 is a conceptual diagram of a graphics processing pipeline that one or more of the PPUs of FIG. 2 can be configured to implement, according to one embodiment of the present invention.

FIG. 4 is a conceptual diagram of a graphics processing pipeline 400, that one or more of the PPUs 202 of FIG. 2 can be configured to implement, according to one embodiment of the present invention. For example, one of the SPMs 310 may be configured to perform the functions of one or more of a vertex processing unit 415, a geometry processing unit 425, and a fragment processing unit 460. The functions of data assembler 410, primitive assembler 420, rasterizer 455, and raster operations unit 465 may also be performed by other processing engines within a GPC 208 and a corresponding partition unit 215. Alternately, graphics processing pipeline 400 may be implemented using dedicated processing units for one or more functions.

Data assembler 410 processing unit collects vertex data for high-order surfaces, primitives, and the like, and outputs the vertex data, including the vertex attributes, to vertex processing unit 415. Vertex processing unit 415 is a programmable execution unit that is configured to execute vertex shader programs, lighting and transforming vertex data as specified by the vertex shader programs. For example, vertex processing unit 415 may be programmed to transform the vertex data from an object-based coordinate representation (object space) to an alternatively based coordinate system such as world space or normalized device coordinates (NDC) space. Vertex processing unit 415 may read data that is stored in L1 cache 320, parallel processing memory 204, or system memory 104 by data assembler 410 for use in processing the vertex data.

Primitive assembler 420 receives vertex attributes from vertex processing unit 415, reading stored vertex attributes, as needed, and constructs graphics primitives for processing by geometry processing unit 425. Graphics primitives include triangles, line segments, points, and the like. Geometry processing unit 425 is a programmable execution unit that is configured to execute geometry shader programs, transforming graphics primitives received from primitive assembler 420 as specified by the geometry shader programs. For example, geometry processing unit 425 may be programmed to subdivide the graphics primitives into one or more new graphics primitives and calculate parameters, such as plane equation coefficients, that are used to rasterize the new graphics primitives.

In some embodiments, geometry processing unit 425 may also add or delete elements in the geometry stream. Geometry processing unit 425 outputs the parameters and vertices specifying new graphics primitives to a viewport scale, cull, and clip unit 450. Geometry processing unit 425 may read data that is stored in parallel processing memory 204 or system memory 104 for use in processing the geometry data. Viewport scale, cull, and clip unit 450 performs clipping, culling, and viewport scaling and outputs processed graphics primitives to a rasterizer 455.

Rasterizer 455 scan converts the new graphics primitives and outputs fragments and coverage data to fragment processing unit 460. Additionally, rasterizer 455 may be configured to perform z culling and other z-based optimizations.

Fragment processing unit 460 is a programmable execution unit that is configured to execute fragment shader programs, transforming fragments received from rasterizer 455, as specified by the fragment shader programs. For example, fragment processing unit 460 may be programmed to perform operations such as perspective correction, texture mapping, shading, blending, and the like, to produce shaded fragments that are output to raster operations unit 465. Fragment processing unit 460 may read data that is stored in parallel processing memory 204 or system memory 104 for use in processing the fragment data. Fragments may be shaded at pixel, sample, or other granularity, depending on the programmed sampling rate.

Raster operations unit 465 is a processing unit that performs raster operations, such as stencil, z test, blending, and the like, and outputs pixel data as processed graphics data for storage in graphics memory. The processed graphics data may be stored in graphics memory, e.g., parallel processing memory 204, and/or system memory 104, for display on display device 110 or for further processing by CPU 102 or parallel processing subsystem 112. In some embodiments of the present invention, raster operations unit 465 is configured to compress z or color data that is written to memory and decompress z or color data that is read from memory.

Color Field Sequential Display

Figure 5A:
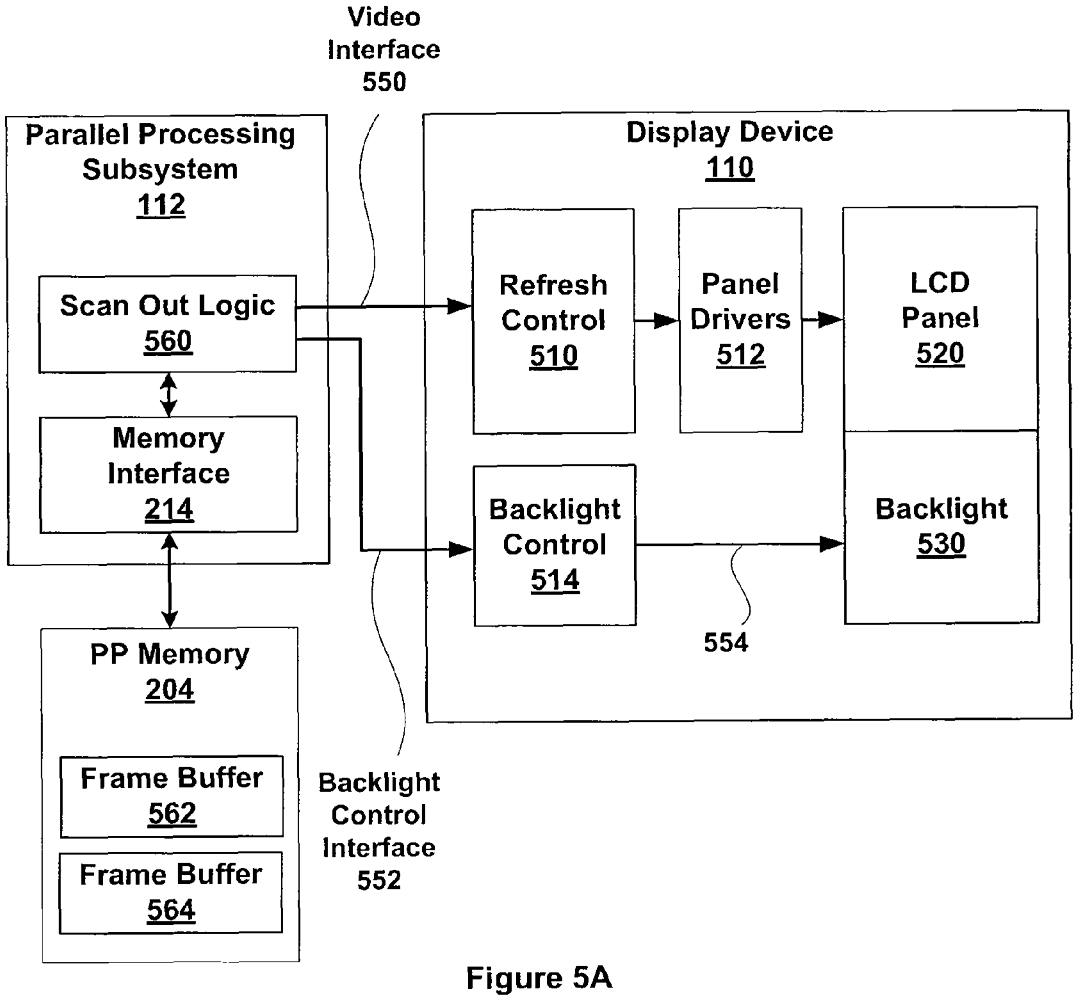
FIG. 5A is a more detailed block diagram of the parallel processing subsystem coupled to a display device, according to one embodiment of the present invention.

FIG. 5A is a more detailed block diagram of the parallel processing subsystem 112 of FIG. 1 coupled to the display device 110, according to one embodiment of the present invention. The parallel processing subsystem 112, described previously, is coupled to PP memory 204 of FIG. 2 via a local memory bus and to the display device 110 via video interface 550. Frame buffer 562 resides in PP memory 204, and stores a frame of video data for display. Scan out logic 560 is coupled to memory interface 214, and is configured to retrieve the video data residing in frame buffer 562 and to transmit the video data via the video interface 550 for display on display device 110. Other frame buffers, such as frame buffer 564, may reside in PP memory 204 as intermediate frames of data. For example, frame buffer 564 may store an image comprising packed red, green, and blue (RGB) intensity values, while frame buffer 562 may store one or more color sub-frames extracted from frame buffer 564. During normal execution, frame buffer 564 may be rendered using any technically feasible technique to include a packed RGB image. Each color channel of the RGB packed image may be extracted to generate one or more images having a single color each that are stored in frame buffer 562. In an alternative embodiment, frame buffers 562 and 564 reside in an on-chip memory within the parallel processing subsystem 112.

The display device 110 comprises refresh control logic 510, panel drivers 512, backlight control circuit 514, an LCD panel 520, and a backlight 530. The refresh control logic 510 is configured to receive data from the video interface 550, and to transpose the data into column and row driver information. In one embodiment, video data is structured as a sequence of rows, where each row includes a sequence of intensity values for one color channel of corresponding pixels comprising the row. The column and row driver information is transmitted to the panel drivers 512, which generate appropriate electrical signals to drive the LCD panel 520. Persons skilled in the art will recognize that any technically feasible gray scale LCD panel, in combination with appropriate refresh control and driver circuits may be used to implement the display device 110 without departing the scope and spirit of the present invention.

The scan out logic 560 retrieves video data from frame buffer 562 and transmits the video data to refresh control logic 510. The video data is structured to include frames comprising one color channel of color pixel information. Each color channel is transmitted as part of a repeating sequence of frames to compose a corresponding color frame over time. For example, the scan out logic 560 may transmit a repeating sequence of a red frame, a green frame, and a blue frame to compose a color frame of RGB pixels. Each frame is displayed as a current display frame for a period of time. A backlight control interface 552 transmits backlight activation information to direct backlight control circuit 514 to illuminate the current display frame with an appropriate backlight color. For example, if the current display frame comprises red color channel information, then the backlight control interface 552 directs the backlight control circuit 514 to illuminate the current display frame with red light. A backlight drive signal 554 comprises individual drive signals for each available color within the backlight 530. When the backlight control interface 552 directs the backlight control circuit 514 to activate a particular color, the backlight control circuit drives one of the individual drive signals within the backlight drive signal 554. In one embodiment, the scan out logic 560 generates control signals for the backlight control interface 552.

The backlight control interface 552 should provide intensity information for driving the selected backlight color. In one embodiment, the intensity information is transmitted to the backlight control circuit 514 via a protocol that encodes a digital intensity value for each available backlight color. For example, a given digital intensity value may comprise a binary number that specifies a target intensity for a specified backlight color. The backlight control circuit 514 generates backlight drive signals 514 based on the digital intensity values. Each individual drive signal comprising the backlight drive signal 554 is attached to one or more light emitting diodes (LEDs) of a corresponding color. A given individual drive signal is asserted to illuminate the one or more attached LEDs to achieve the target intensity as an average intensity value. A first technique implements fixed-frequency pulse width modulation (PWM), whereby the duty cycle of a high-frequency signal is adjusting in proportion to the target intensity. In this context, high-frequency means a frequency greater than a prevailing frame refresh frequency. A second technique implements proportional pulse width modulation, whereby the width of a single pulse of light per frame is adjusted in proportion to the target intensity. In the above two techniques, associated LEDs are driven fully on or fully off. A third technique implements proportional pulse current modulation, whereby associated LEDs are turned on continuously for the duration of a corresponding frame and then off. The current passing through the LEDs is adjusted according to the target intensity. Three different exemplary techniques have been discussed above, however, any technically feasible technique may be implemented to drive the attached LEDs to a target average intensity without departing the scope and spirit of the present invention.

In an alternative embodiment, the backlight control interface 552 comprises a set of signals corresponding directly to the individual drive signals of the backlight drive signal 554. Persons skilled in the art will understand that the first and second techniques describe above for driving LEDs to a target intensity may be implemented using the backlight control circuit 514 as current and voltage translation amplifier for driving the LEDs.

Figure 5B:
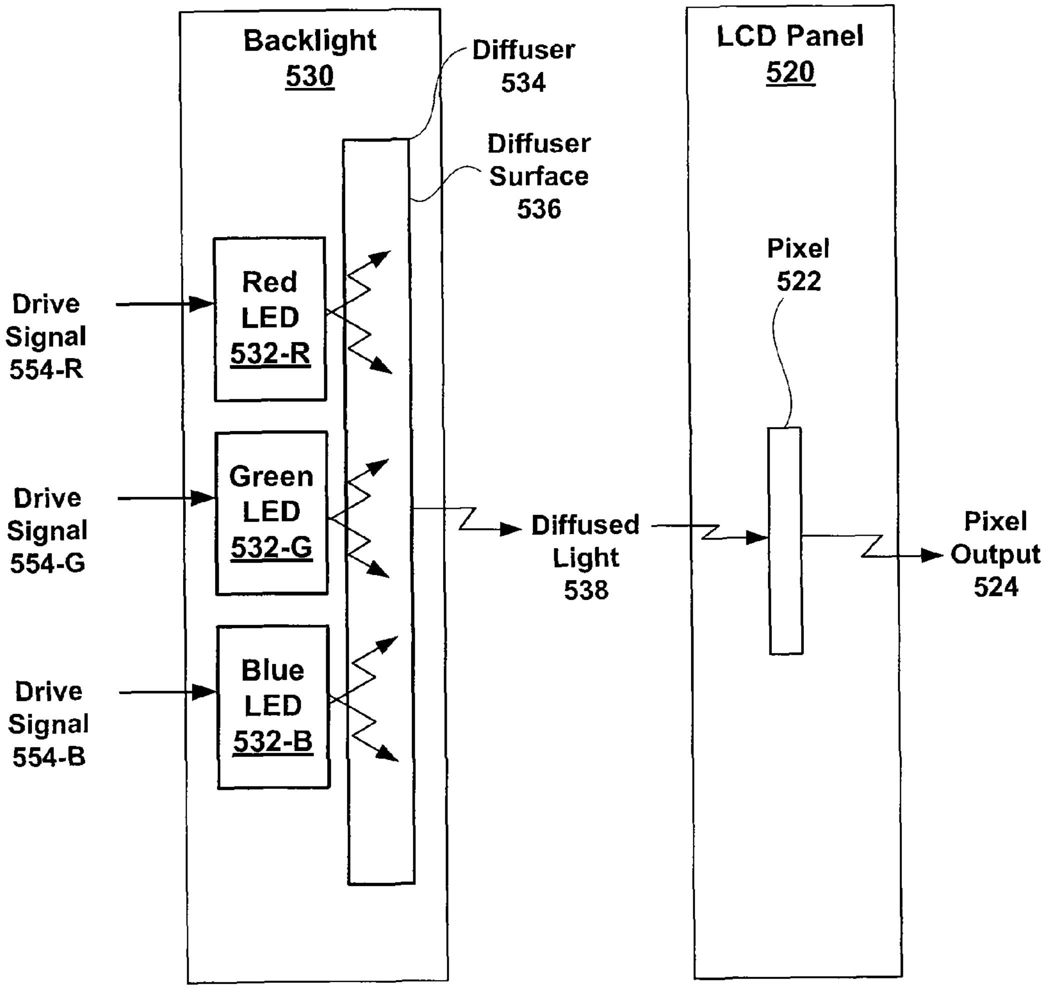
FIG. 5B is a conceptual diagram of an optical path from a backlight to a single pixel output, according to one embodiment of the present invention.

FIG. 5B is a conceptual diagram of an optical path from the backlight 530 to a single pixel output 524, according to one embodiment of the present invention. The backlight 530 comprises a red LED 532-R, a green LED 532-G, and a blue LED 532-B. Each LED 530 may comprise an arbitrary number of individual LED elements. Drive signals 554 comprise the individual drive signals of FIG. 5A. When a drive signal 554 is asserted, the corresponding LED 532 generates illumination of a corresponding color. A diffuser 534 distributes the illumination to produce a substantially even light flux emission at the diffuser surface 536. Diffused light 538 from the diffuser surface 536 illuminates a pixel 522 within the LCD panel. Optical transmission for the pixel 522 is modulated to generate a pixel output light 524 having a controlled intensity. A color for the pixel 522 is produced through perception-based temporal integration of red light from the red LED 532-R that is intensity modulated by the pixel 522, green light from the green LED 532-G that is intensity modulated by the pixel 522, and blue light from the blue LED 532-B that is intensity modulated by the pixel 522.

Figure 6A:
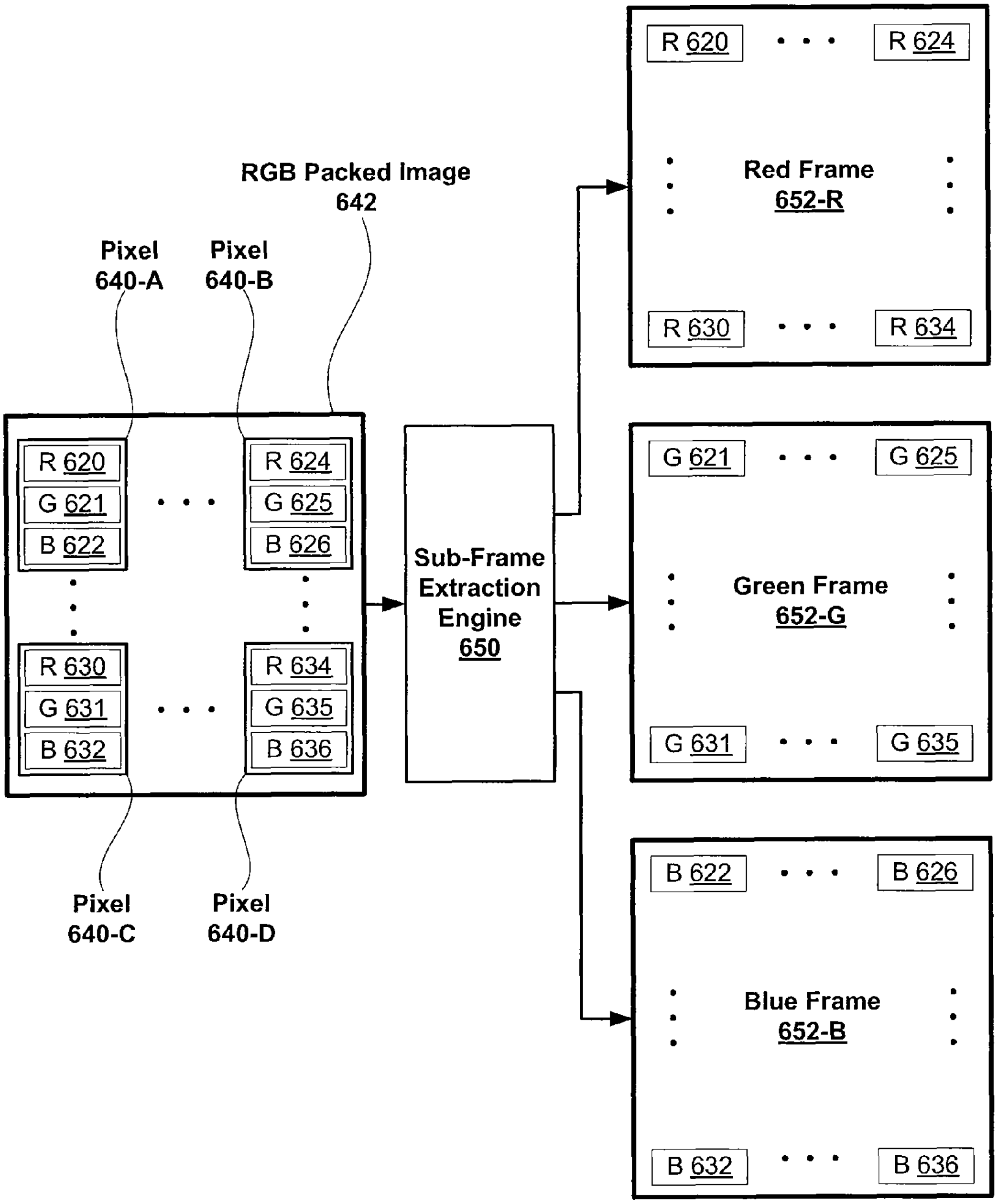
FIG. 6A is a conceptual diagram of sub-frame extraction into different frames for display, according to one embodiment of the present invention.

FIG. 6A is a conceptual diagram of sub-frame extraction into different frames 652 for display, according to one embodiment of the present invention. An RGB packed image 642 residing in a frame buffer, such as frame buffer 562 of FIG. 5A, comprises pixels having red, green, and blue color channels. For example, pixel 640-A comprises red channel component R 620, green channel component G 621, and blue channel component B 622. Similarly, pixel 640-B comprises color channel components R 624, G 625, and B 626, and so forth. In certain embodiments, each pixel also includes an alpha color channel, used to indicate opacity (1-transparency). Persons skilled in the art will understand that any other attributes may also be associated with each pixel without departing the scope of the present invention.

A sub-frame extraction engine 650 is configured to extract color channel components from the RGB packed image 642 and to write the color channel components to a corresponding color frame 652. In one embodiment, a red frame 652-R is allocated to store red channel components, a green frame 652-G is allocated to store green channel components, and a blue frame 652-B is allocated to store blue channel components. The sub-frame extraction engine 650 copies red channel components including R 620, R 624, R 630, and R 634 to red frame 652-R. Similarly, the sub-frame extraction engine 650 copies green channel components including G 621, G 625, G 631, and G 635 to green frame 652-G, and blue channel components including B 622, B 626, B 632, and B 636 to blue frame 652-B. Each of the color frames 652 is read by the scan out logic 560 and transmitted in sequence via the video interface 550 to the display device 110. In alternative embodiments, the sub-frame extraction engine 650 is configured to perform color space conversion between different color spaces. For example, the sub-frame extraction engine 650 may extract CMY (cyan, magenta, yellow) color from a packed image to generate the red frame 652-R, the green frame 652-G, and the blue frame 652-B. In another example, the sub-frame extraction engine 650 extracts RGB packed image 642 to generate red, green, blue, and yellow frames 652 for display.

In one embodiment, color channel component data for a target color channel is copied to a corresponding target color frame 652 by reading pixel data for a pixel 640, shifting the pixel data to a position corresponding to a target position in the target color frame 652, and performing a bit-wise masked write operation to the target color frame 652. In another embodiment, a word comprising four bytes of target color channel information is accumulated before being written to the respective color frame 652. For example, if each color channel component comprises one byte of data, then four bytes of target color channel data are extracted and accumulated for each color channel before being written to respective color frames 652. In other words, four bytes of red color channel data are extracted along a row from the RGB packed image 642 before being written as a whole four byte word to red frame 652-R. Similarly, four bytes of green color channel data are extracted from RGB packed image 642 before being written as a whole four byte word to green frame 652-G, and so forth.

In one embodiment, the sub-frame extraction engine 650 is implemented as a shader program, configured to execute as a thread or thread group on at least one GPC 208 within the parallel processing subsystem 112. In another embodiment, the sub-frame extraction engine 650 is implemented using hardware circuitry within the scan out logic 560. Persons skilled in the art will understand that the sub-frame extraction engine 650 may be implemented using any technically feasible techniques without departing the scope and spirit of the present invention.

Figure 6B:
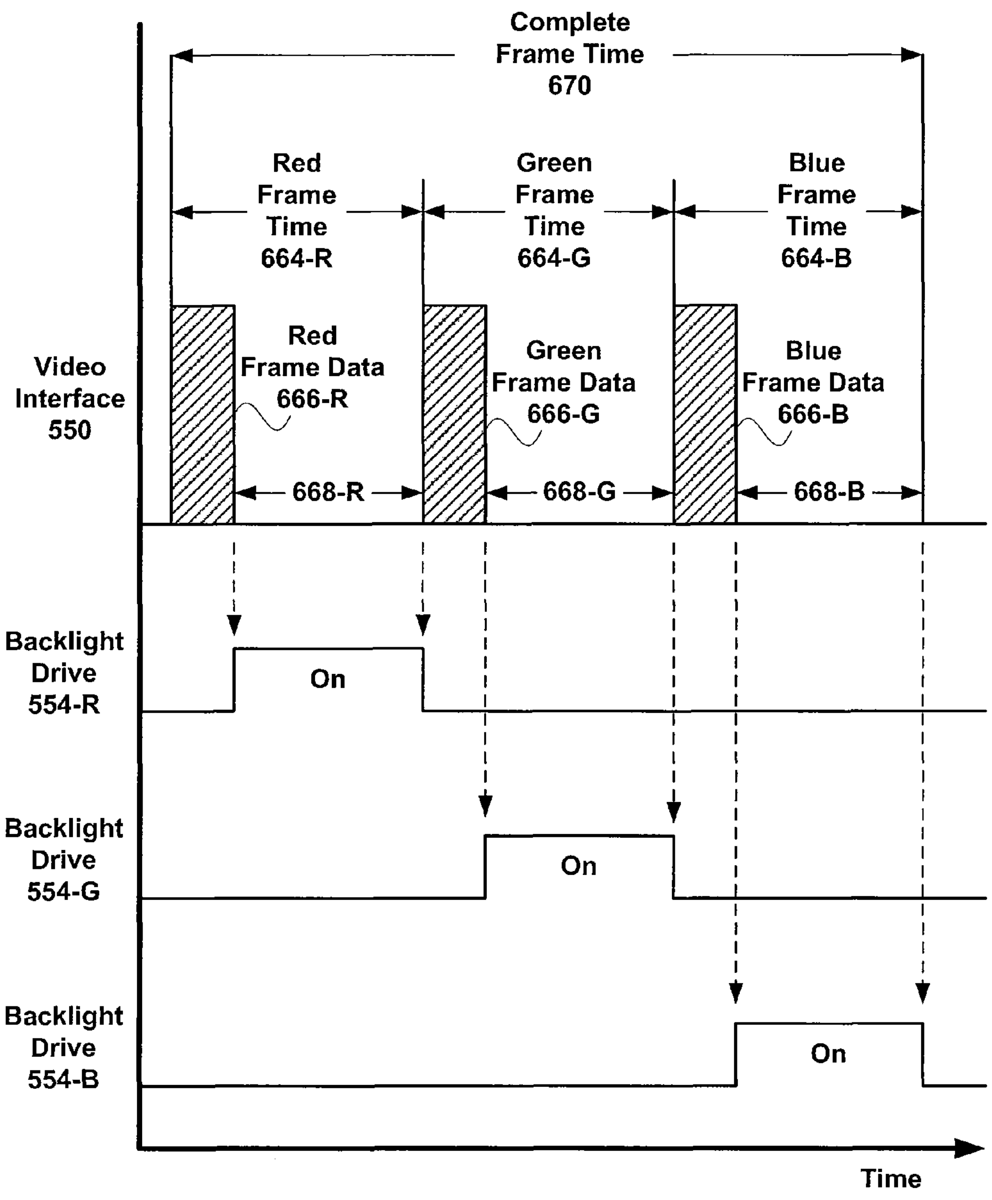
FIG. 6B illustrates scan out timing of different color frames for display, according to one embodiment of the present invention.

FIG. 6B illustrates scan out timing of different color frames 664 for display, according to one embodiment of the present invention. Red frame 652-R is displayed during red frame time 664-R, green frame 652-G is displayed during green frame time 664-G, and blue frame 652-B is displayed during blue frame time 664-B. A complete frame time 670 defines the duration for one complete frame of RGB data. Each backlight color is driven to correspond in time with an associated frame time 664. The backlight drive 554-R of FIG. 5B enables red LED 532-R to illuminate during red frame time 664-R. The backlight drive 554-G enables green LED 532-G to illuminate during green frame time 664-G. The backlight drive 554-B enables blue LED 532-B to illuminate during blue frame time 664-B. In this way, each color frame time 664 is illuminated by an appropriate color of backlight illumination. In one embodiment, the three LEDs 532 are driven to illuminate a common target average intensity. In alternative embodiments, each one of the three LEDs 532 is driven to illuminate an individual intensity value.

In one embodiment, red frame data 666-R corresponding to red frame 652-R is transmitted via the video interface 550 of FIG. 5A during a time period that is smaller than the red frame time 664-R. An image on the LCD panel 520 is updated while red frame data 666-R is transmitted to the LCD panel 520. During this time, data for a previous blue frame may be overwritten with the red frame data 666-R. A red display time 668-R represents a span of time in which the red frame data 666-R is displayed on LCD panel 520 without any update activity to the LCD panel 520. In one embodiment, backlight drive 554-R is active ("on"), as shown, during the red display time 668-R, and off otherwise. The backlight drive 554-R may be modulated to achieve the target average intensity, as discussed previously. In an alternative embodiment, the backlight drive 554-R is active during at least a portion of the time period in which red frame data 666-R is transmitted to the LCD panel 520. The backlight drive 554-R may be modulated in such an alternative embodiment to achieve the target average intensity, as discussed previously. Additionally, the green frame date 666-G is transmitted via the video interface 550 during a time period that is smaller than green frame time 664-G, and the blue frame data 666-B is transmitted during a time period that is smaller than the blue frame time 664-B. Furthermore, backlight drives 554-G and 554-B are driven according to the above description for backlight drive 554-R.

Each frame buffer configured to store red frame data 666-R, green frame data 666-G, and blue frame data 666-B is allocated and managed as a separate frame of data for display. In certain embodiments, parallel processing subsystem 112 is required to manage three independent frame buffers to store data for each color channel extracted via sub-frame extraction from one packed RGB frame buffer. The complexity associated with managing and coordinating three independent frame buffers for display can be eliminated by instead generating one frame of data comprising red, green, and blue fields, as described below in FIGS. 7A and 7B.

Figure 7A:
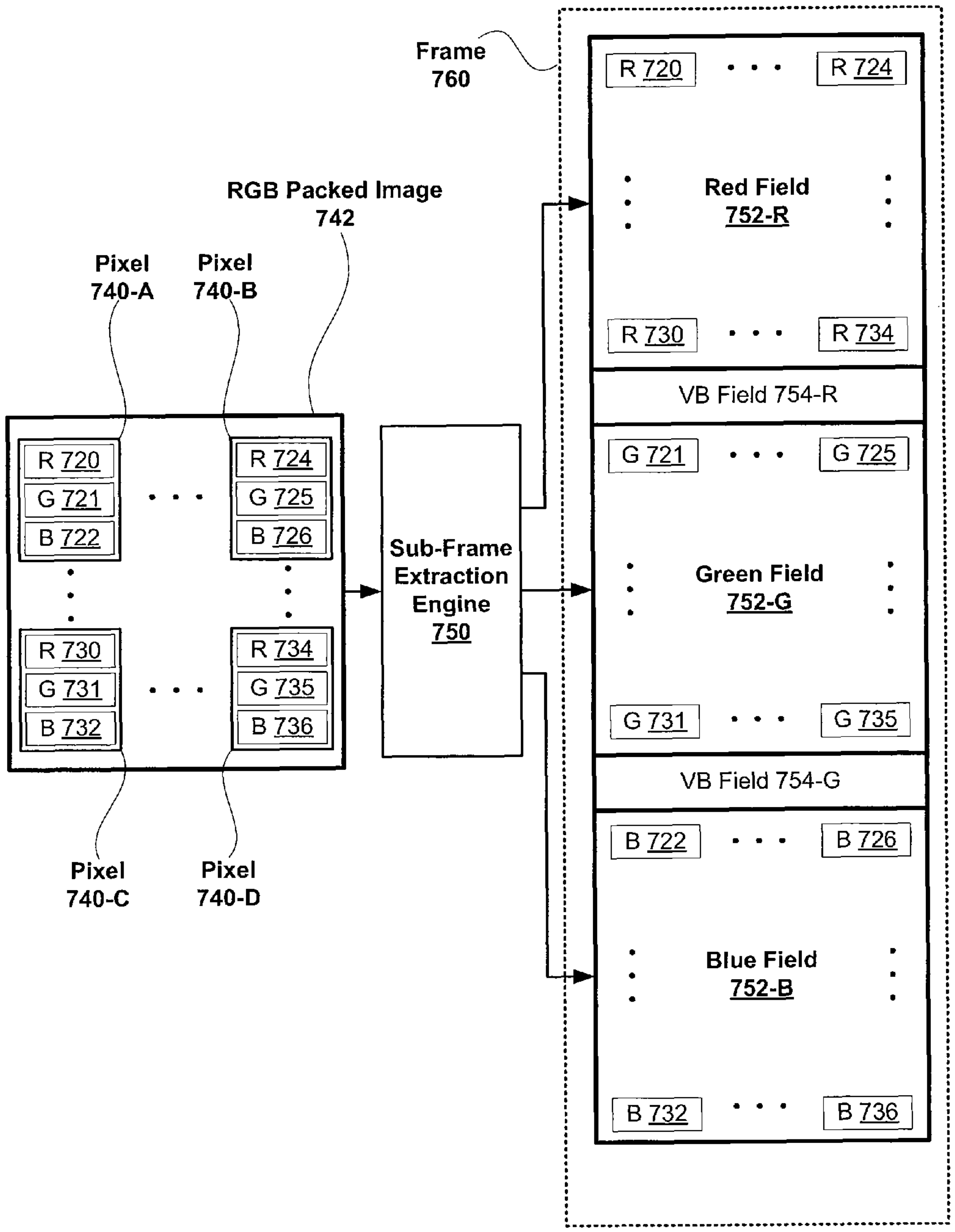
FIG. 7A is a conceptual diagram of sub-frame extraction into different fields of a single frame for display, according to one embodiment of the present invention.

FIG. 7A is a conceptual diagram of sub-frame extraction into different fields of a single frame for display, according to one embodiment of the present invention. An RGB packed image 742 residing in a frame buffer, such as frame buffer 562 of FIG. 5A, comprises pixels having red, green, and blue color channels. For example, pixel 740-A comprises red channel component R 720, green channel component G 721, and blue channel component B 722. Similarly, pixel 740-B comprises color channel components R 724, G 725, and B 726, and so forth. In certain embodiments, each pixel also includes an alpha color channel, used to indicate opacity (1-transparency). Persons skilled in the art will understand that any other attributes may also be associated with each pixel without departing the scope of the present invention.

A sub-frame extraction engine 750 is configured to extract color channel components from the RGB packed image 742 and to write the color channel components to a corresponding color field 752 within frame 760. The frame 760 comprises a red field 752-R, a green field 752-G, and a blue field 752-B. The frame 760 may also comprise a vertical blanking (VB) field 754-R, and a VB field 754-G. In alternative embodiments, the sub-frame extraction engine 750 is configured to perform color space conversion between different color spaces. For example, the sub-frame extraction engine 750 may extract CMY color from a packed image to generate the red field 752-R, the green field 752-G, and the blue field 752-B. In another example, the sub-frame extraction engine 750 extracts RGB packed image 742 to generate red, green, blue, and yellow fields 652 for display.

The sub-frame extraction engine 750 copies red channel components including R 720, R 724, R 730, and R 734 to red field 752-R within frame 760. Similarly, the sub-frame extraction engine 750 copies green channel components including G 721, G 725, G 731, and G 735 to green field 752-G, and blue channel components including B 722, B 726, B 732, and B 736 to blue field 752-B. The red field 752-R, VB field 754-R, green field 752-G, VB field 754-G, and blue filed 752-B are read by the scan out logic 560 and transmitted in sequence as frame 760 via the video interface 550 to the display device 110. A vertical blanking state is asserted during the VB field 754-R, VB field 754-G, and a vertical blanking time subsequent to the blue field 752-B.

In one embodiment, color channel component data for a target color channel is copied to a corresponding target color field 752 by reading pixel data for a pixel 740, shifting the pixel data to a position corresponding to a target position in the target color field 752 within frame 760, and performing a bit-wise masked write operation to the target color field 752. In another embodiment, a word comprising four bytes of target color channel information is accumulated before being written to the respective color field 752. For example, if each color channel component comprises one byte of data, then four bytes of target color channel data are extracted and accumulated for each color channel before being written to respective color fields 752. In other words, four bytes of red color channel data are extracted along a row from the RGB packed image 742 before being written as a whole four byte word to red field 752-R. Similarly, four bytes of green color channel data are extracted from RGB packed image 742 before being written as a whole four byte word to green field 752-G, and so forth.

In one embodiment, the sub-frame extraction engine 750 is implemented as a shader program, configured to execute as a thread or thread group on at least one GPC 208 within the parallel processing subsystem 112. In another embodiment, the sub-frame extraction engine 750 is implemented using hardware circuitry within the scan out logic 560. Persons skilled in the art will understand that the sub-frame extraction engine 750 may be implemented using any technically feasible techniques without departing the scope and spirit of the present invention.

Figure 7B:
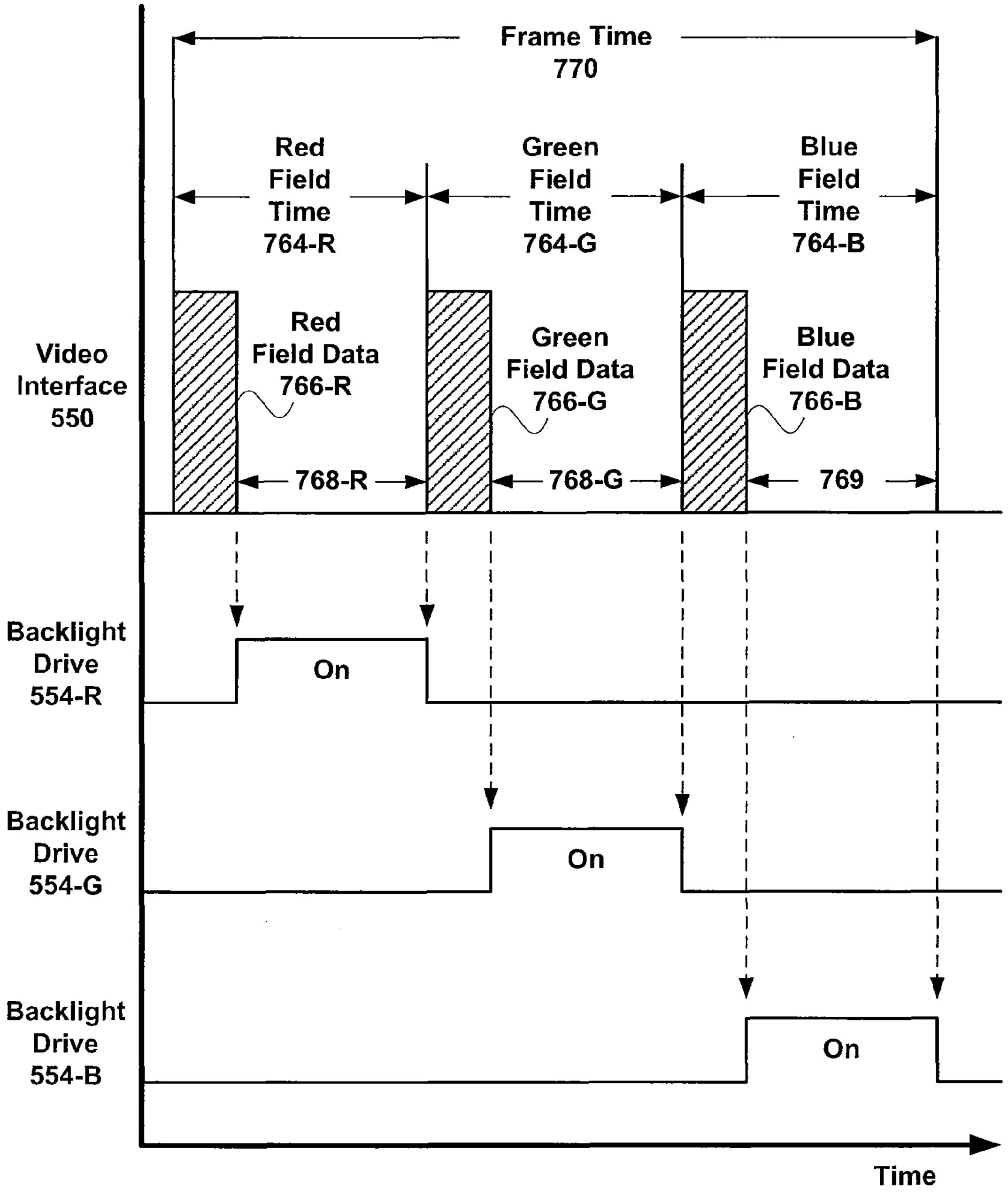
FIG. 7B illustrates scan out timing of different color fields within the single frame for display, according to one embodiment of the present invention.

FIG. 7B illustrates scan out timing of different color fields within the single frame 760 for display, according to one embodiment of the present invention. Data associated with red field 752-R from frame 760 is displayed during red field time 764-R, data associated with the green field 752-G is displayed during green field time 764-G, and data associated with blue field 752-B is displayed during blue field time 764-B. A frame time 770 defines a duration for one complete frame of RGB data. Each backlight color is driven to correspond in time with an associated frame time 764. The backlight drive 554-R of FIG. 5B enables red LED 532-R to illuminate during red field time 764-R. The backlight drive 554-G enables green LED 532-G to illuminate during green field time 764-G. The backlight drive 554-B enables blue LED 532-B to illuminate during blue field time 764-B. In this way, each color field time 764 is illuminated by an appropriate color of backlight illumination. In one embodiment, the three LEDs 532 are driven to illuminate according to a common target average intensity. In alternative embodiments, each one of the three LEDs 532 is driven to illuminate according to an individual intensity value.

In one embodiment, red field data 766-R corresponding to red field 752-R is transmitted via the video interface 550 of FIG. 5A during a time period that is smaller than the red field time 764-R. An image on the LCD panel 520 is updated while red field data 766-R is transmitted to the LCD panel 520. During this time, data for a previous blue field may be overwritten with the red field data 766-R. A vertical blanking time 768-R represents a span of time in which the red field data 766-R is displayed on LCD panel 520 without any update activity to the LCD panel 520. In one embodiment, backlight drive 554-R is active ("on"), as shown, during the vertical blanking time 768-R, and off otherwise. The backlight drive 554-R may be modulated to achieve the target average intensity, as discussed previously. In an alternative embodiment, the backlight drive 554-R is active during at least a portion of the time period in which red frame data 766-R is transmitted to the LCD panel 520. The backlight drive 554-R may be modulated in such an alternative embodiment to achieve the target average intensity, as discussed previously. Additionally, the green field date 766-G is transmitted via the video interface 550 during a time period that is smaller than green field time 764-G, and the blue field data 766-B is transmitted during a time period that is smaller than the blue field time 764-B. Furthermore, backlight drives 554-G and 554-B are driven according to the above description for backlight drive 554-R. In certain embodiments, the backlight drives 554 are enabled in time alignment with display times for each corresponding color field time 764 to maximize illumination time within the color field time 764, while optionally accounting for data transmission time for the color field data 766.

In one embodiment, each unit of data transmitted via the video interface 550 is associated with a particular clock transition on a pixel clock. Color field data 766 is transmitted at a very high speed, involving correspondingly rapid clock transitions, so that color field data 766 takes approximately half or less of the color field time 764. The goal is to generally maximize vertical blanking time 768, to facilitate a maximum backlight "on" time for each field time 764. To reduce storage associated with VB fields 754 within frame 760, the time per clock transition is increased significantly (the pixel clock is slowed significantly), so that VB fields 754 need only occupy a small number of lines of data. For example, if each VB field 754 includes five lines of data, then the pixel clock may need to be slowed down sufficiently to require a majority of field time 764 for transmission. Upon transmission of VB field 754, the pixel clock is sped up for transmission of color field data 766.

One frame buffer is needed to store frame 760, comprising red field 752-R, green field 752-G, and blue field 752-B. The complexity associated with managing and coordinating three independent frame buffers for display is therefore eliminated by instead generating and managing only one frame of data for display from each unique RGB packed frame.

Figure 8:
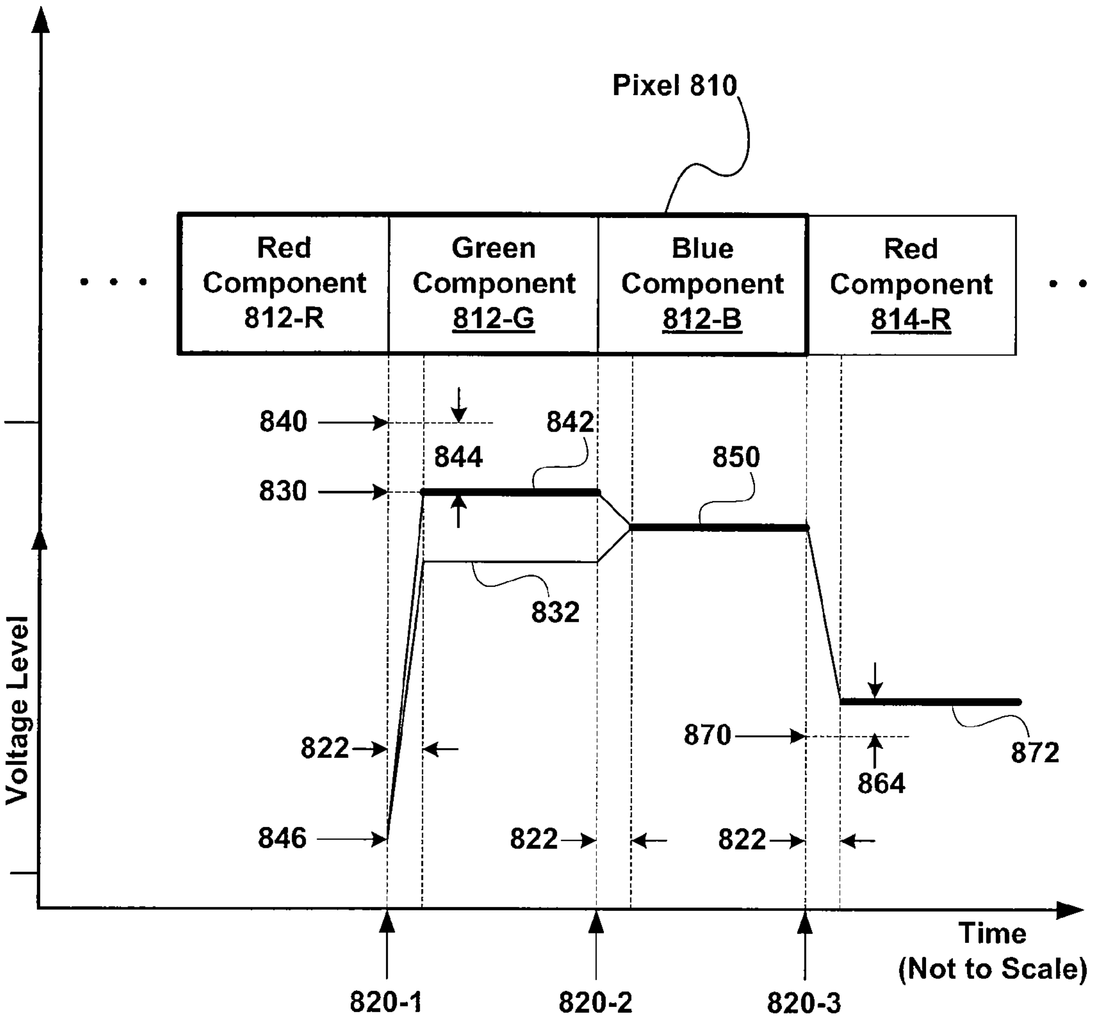
FIG. 8 illustrates pixel compensation according to one embodiment of the present invention.

FIG. 8 illustrates pixel compensation according to one embodiment of the present invention. An LCD device, such as LCD panel 520, comprises a two-dimensional array of pixels that store a current image as voltage values associated a capacitive structure residing in each pixel. Each voltage value corresponds to an intensity value for the associated pixel. To update the current image, rows of pixels are sequentially enabled to be written with new voltage values per pixel in a frame refresh process. Each new voltage value is applied to a corresponding capacitive structure, which charges asymptotically to the new voltage value. As the frame refresh process is sped up, for example to maximize vertical blanking time 768 of FIG. 7B, the capacitive structure for each pixel must charge to a target voltage more quickly. However, inherent time constants, such as a resistive-capacitive (RC) constant, associated with physical structures of the LCD device limit how quickly each capacitive structure can charge to a target voltage. The actual voltage attained within the capacitive structure during the frame refresh process for a new image is a function of the current voltage of the capacitive structure, a new target voltage, and any inherent time constants for the LCD device.

For conventional packed RGB LCD devices, the new target voltage tends to be similar in value to the current voltage because the two voltages are associated with the same color channel. As such, charging to the new target voltage is trivially attained, except briefly in uncommon cases here adjacent frames are completely different. However, in color field sequential LCD displays, the current and new target voltages are typically quite different because they correspond to different color channels of an associated pixel. As such, each color channel of each image introduces de-correlated inter-frame interference noise in the new target voltage. This noise degrades image quality by adding chromatic ghosting to every frame.

Sequential color components displayed for one pixel on LCD panel 520 are illustrated as red component 812-R, green component 812-G, blue component 812-B, and red component 814-R. Pixel 810 comprises color components 812-R, 812-G, and 812-B. Frame boundaries 820 are indicated along a time axis. Frame boundary 820-1 indicates the start of a frame of green color channel data displayed by the pixel. The capacitive structure within the pixel is charged to a new voltage during line refresh time 822. The new target voltage level corresponding to the green component 812-G is indicated as voltage 842.

An uncompensated column drive voltage 830 is set to the new target voltage 842, given by the green component 812-G of the pixel. As shown, however, line refresh time 822 is inadequate to properly charge the capacitive structure in the pixel. Instead of charging to the new target voltage 842, the capacitive structure charges to an undershoot voltage of 832. A compensation offset 844 is computed to account for initial voltage 846, line refresh time 822, and new target voltage 842. The compensation offset 844 is used to generate compensated column drive voltage 840. Driving the capacitive structure with compensated column drive voltage 840 instead of uncompensated drive voltage 830 allows the capacitive structure to attain new target voltage 842 within line refresh time 822. New target voltage 850 is relatively close to new target voltage 842, so undershoot is less significant. A compensation offset for new target voltage 850 would therefore be relatively small. Compensation offset 864 is computed based on at least new target voltage 850 and new target voltage 872. Compensated column drive voltage 870 is used to charge the capacitive structure to new target voltage 872, corresponding to an intensity for red component 814-R.

In one embodiment, a lookup table is used to compute a compensation offset based on a current voltage and a new target voltage. A compensated column drive voltage is generated based on the compensation offset and the new target voltage. The current voltage corresponds to an intensity value stored in a previously displayed frame of data, while the new target voltage corresponds to an intensity value in a new frame being scanned out for display. The scan out logic 560 of FIG. 5A accesses the previously displayed frame of data and the new frame of data to compute compensated intensity values for transmission via video interface 550. The compensated intensity values correspond to compensated column drive voltages that may be used to drive LCD panel 510. Any technically feasible function implemented in the lookup table or directly computed may be used to compute the compensated intensity values without departing the scope of the present invention.

Figure 9:
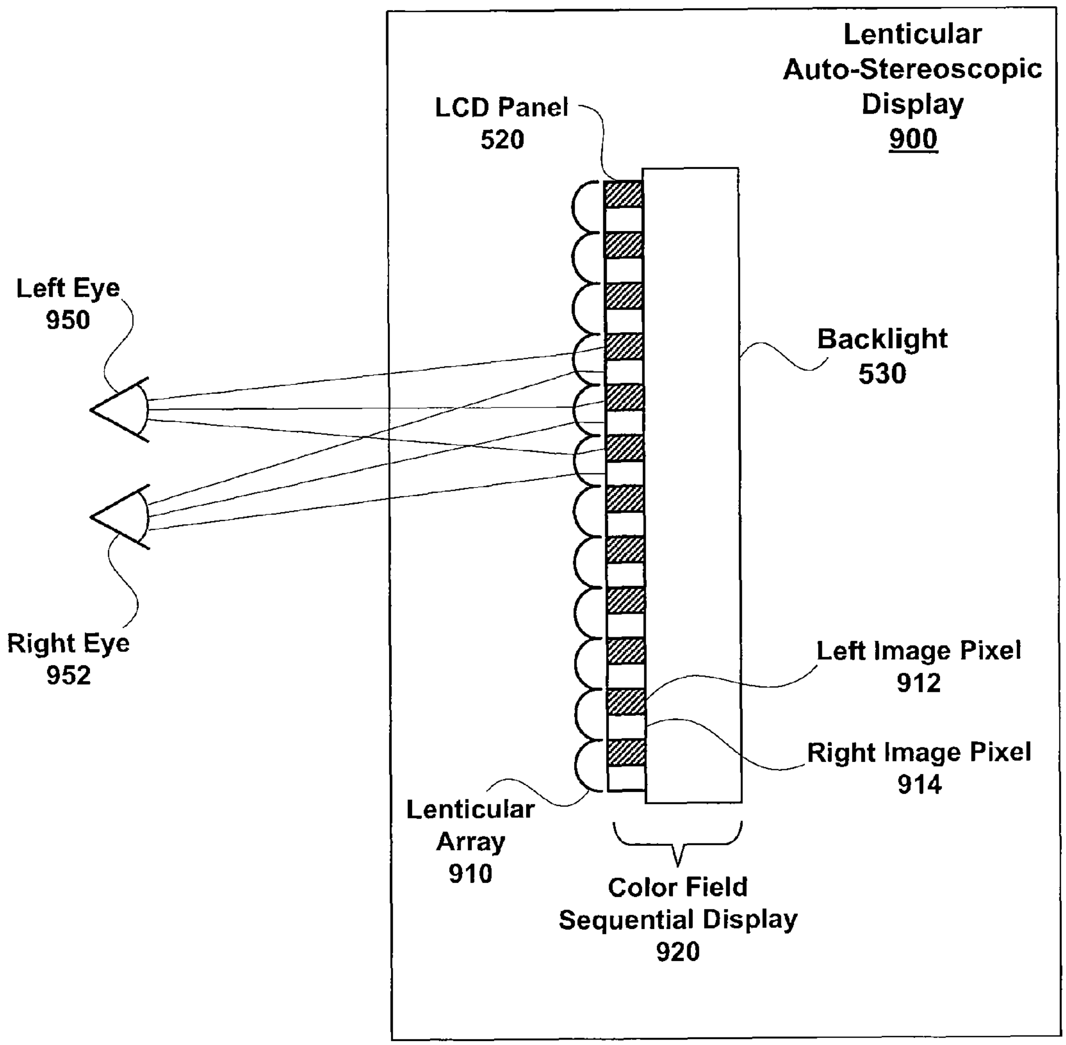
FIG. 9 is a conceptual diagram of a lenticular auto-stereoscopic display based on a color field sequential display, according to one embodiment of the present invention.

FIG. 9 is a conceptual diagram of a lenticular auto-stereoscopic display 900 based on a color field sequential display 920, according to one embodiment of the present invention. The lenticular auto-stereoscopic display 900 comprises the color field sequential display 920 and a lenticular array 910. The color field sequential display 920 comprises backlight 530 of FIGS. 5A-5B, LCD panel 520, and related drive circuitry depicted in FIG. 5A. The leticular array 910 is configured to selectively direct light from adjacent pixels within the LCD along different viewing angles. Persons skilled in the art will understand that an observer having a left eye 950 and a right eye 952 is able to receive a different image in each eye, thereby simulating stereo vision of an object being displayed on the color field sequential display 920. A left image (depicted using shaded pixels) displayed on the color field sequential display 920 is directed to the observer's left eye 950 and a right image (depicted using un-shaded pixels) is directed to the observer's right eye 952. For example, left image pixel 912 is directed to the observer's left eye 950, while right image pixel 914 is directed to the observer's right eye 952.

One advantage of the lenticular auto-stereoscopic display 900 over prior art solutions based on packed RGB display technologies is that chromatic fringing from image sensitivity to fine spatial differences between adjacent RGB sub-pixel color channel elements does not exist in the color field sequential display 920. As a result, the lenticular auto-stereoscopic display 900 provides a superior image over prior art solutions that suffer from chromatic fringing effects.

In one embodiment, the lenticular auto-stereoscopic display 900 is supplied with color channel frames 652, as described previously in FIGS. 6A-6B. The color channel frames 652 may comprise compensated intensity values, as described previously in FIG. 8. In another embodiment, the lenticular auto-stereoscopic display 900 is supplied with frames comprising color channel fields 752, as described previously in FIGS. 7A-7B. The color channel fields 752 may comprise compensated intensity values, as described previously in FIG. 8.

Figure 10:
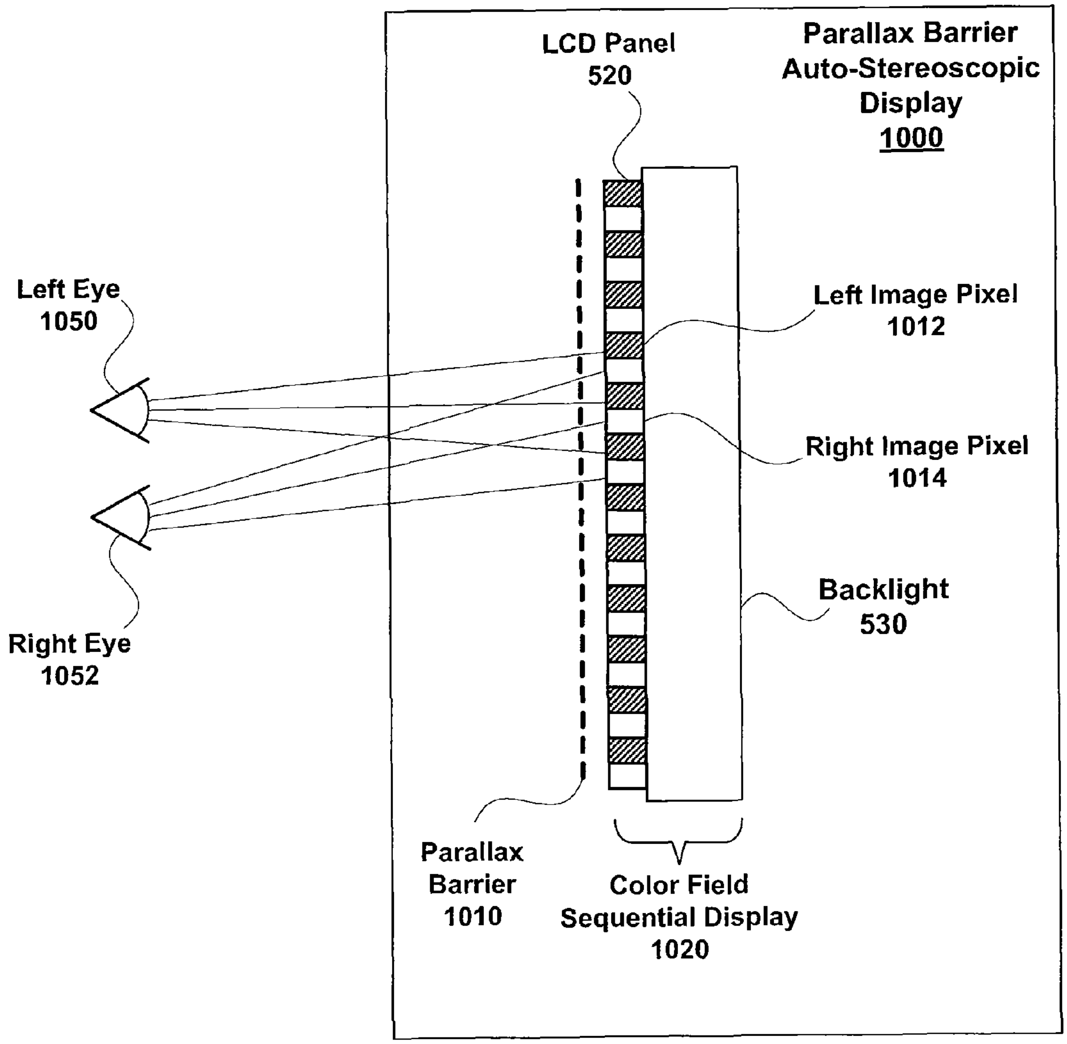
FIG. 10 is a conceptual diagram of a parallax barrier auto-stereoscopic display based on a color field sequential display, according to one embodiment of the present invention.

FIG. 10 is a conceptual diagram of a parallax barrier auto-stereoscopic display 1000 based on a color field sequential display, according to one embodiment of the present invention. The parallax-barrier auto-stereoscopic display 1000 comprises the color field sequential display 1020 and a parallax barrier 1010. The color field sequential display 1020 comprises backlight 530 of FIGS. 5A-5B, LCD panel 520, and related drive circuitry depicted in FIG. 5A. The parallax barrier 1010 is configured to selectively block light from adjacent pixels within the LCD for different viewing angles. Persons skilled in the art will understand that an observer having a left eye 1050 and a right eye 1052 is able to see a different image in each eye, thereby simulating stereo vision of an object being displayed on the color field sequential display 1020. A left image (depicted using shaded pixels) displayed on the color field sequential display 1020 is visible to the observer's left eye 1050 but not the observer's right eye 1052. Similarly, a right image (depicted using un-shaded pixels) is visible to the observer's right eye 1052 but not the observer's left eye 1050. For example, left image pixel 1012 is visible to the observer's left eye 1050, while right image pixel 1014 is visible to the observer's right eye 1052. In one embodiment parallax barrier 1010 comprises a liquid crystal screen that may be actively turned on (opaque) to operate in auto-stereoscopic mode or off (transparent) to operate in a conventional non-stereoscopic mode.

One advantage of the parallax-barrier auto-stereoscopic display 1000 over prior art solutions based on packed RGB display technologies is that chromatic fringing from image sensitivity to fine spatial differences between adjacent RGB sub-pixel elements does not give exist in the color field sequential display 1020. As a result, the parallax-barrier auto-stereoscopic display 1000 provides a superior image over prior art solutions that suffer from chromatic fringing effects.

In one embodiment, the parallax-barrier auto-stereoscopic display 1000 is supplied with color channel frames 652, as described previously in FIGS. 6A-6B. The color channel frames 652 may comprise compensated intensity values, as described previously in FIG. 8. In another embodiment, the parallax-barrier auto-stereoscopic display 1000 is supplied with frames comprising color channel fields 752, as described previously in FIGS. 7A-7B. The color channel fields 752 may comprise compensated intensity values, as described previously in FIG. 8.

Figure 11:
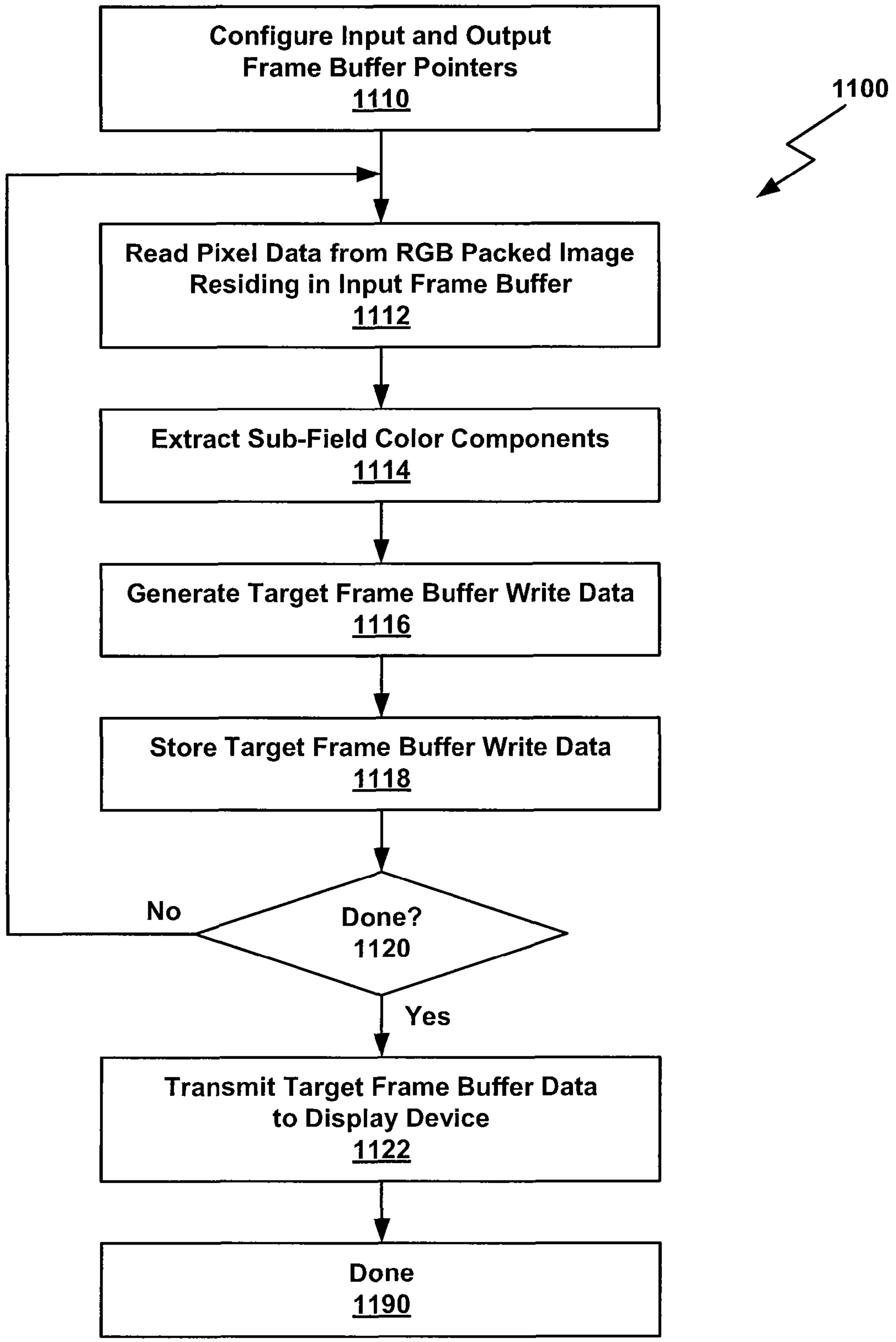
FIG. 11 is a flow diagram of method steps for performing sub-frame extraction, according to one embodiment of the present invention.

FIG. 11 is a flow diagram of method steps 1100 for performing sub-frame extraction, according to one embodiment of the present invention. Although the method steps are described in conjunction with the systems of FIGS. 1-7B, and 9-10, persons skilled in the art will understand that any system configured to perform the method steps, in any order, is within the scope of the invention.

The method begins in step 1110, where a sub-frame extraction engine configures pointers for input and output frame buffers. In one embodiment, sub-field extraction engine 750 configures one input frame buffer pointer to point to an RGB packed frame of data, and one output frame buffer pointer to point to a frame of data comprising a red color field, a green color field, and a blue color field. In another embodiment, sub-field extraction engine 650 configures one input frame buffer pointer to point to the RGB packed frame of data, and one red output frame buffer pointer to a frame of red data, one green output frame buffer pointer to a frame of green data, and one blue output frame buffer pointer to a frame of blue data.

In step 1112, the sub-frame extraction engine reads pixel data from the RGB packed frame of data residing in the input frame buffer. The pixel data comprises at least one red, one green, and one blue color component. In step 1114, the sub-frame extraction engine extracts and separately buffers each color component of the pixel data. In step 1116, the sub-frame extraction engine generates target frame buffer write data. In one embodiment, the target frame buffer write data comprises an offset unit of data, such as a byte, of color channel data and a corresponding write mask for each color channel. In another embodiment, the target frame buffer write data comprises a set of units of color channel data for each color channel. For example, the target frame buffer write data may comprise four byes of color channel data, where each byte represents color channel data for one input pixel.

In step 1118, the sub-frame extraction engine stores the target frame buffer write data. In one embodiment, the target frame buffer write data is stored within color channel fields of one frame of data. The color channel fields may be located within the target frame buffer as offsets from the output frame buffer pointer. In another embodiment, the target frame buffer write data is stored into individual frames of data. For example, target frame buffer write data for a red color channel is stored at a location determined by the red output frame buffer pointer, target frame buffer write data for a green color channel is stored at a location determined by the green output frame buffer pointer, and so forth.

If, in step 1120, the sub-frame extraction engine has not extracted sub-field pixel data for each pixel of the RGB packed frame of data, then the method proceeds back to step 1112. However, if the sub-frame extraction engine has extracted sub-field pixel data for each pixel of the RGB packed frame of data, then the method proceeds to step 1122.

In step 1122, the scan out logic 560 of FIG. 5A transmits target frame buffer data to the display device 110 of FIG. 1. In one embodiment, the scan out logic 560 transmits the one frame of data. The scan out logic 560 may configure an associated pixel clock to extend a vertical blank period associated with a boundary between fields within the one frame of data. In an alternative embodiment, the scan out logic 560 sequentially transmits the frame of red data, the frame of green data, and the frame of blue data. The scan out logic 560 is configured to activate an illumination color from backlight 530 that corresponds to a currently displayed color channel. For example, when the frame of red data is being displayed on LCD panel 520, the backlight 530 is configured to generate red illumination. When the frame of green data is being displayed on LCD panel 520, the backlight 530 is configured to generate green illumination, and so forth. The method terminates in step 1190.

The method steps 1100 may be repeated for each new RGB packed frame of data. Persons skilled in the art will recognize that different techniques may be implemented for buffer management without departing the scope and spirit of the invention.

Figure 12:
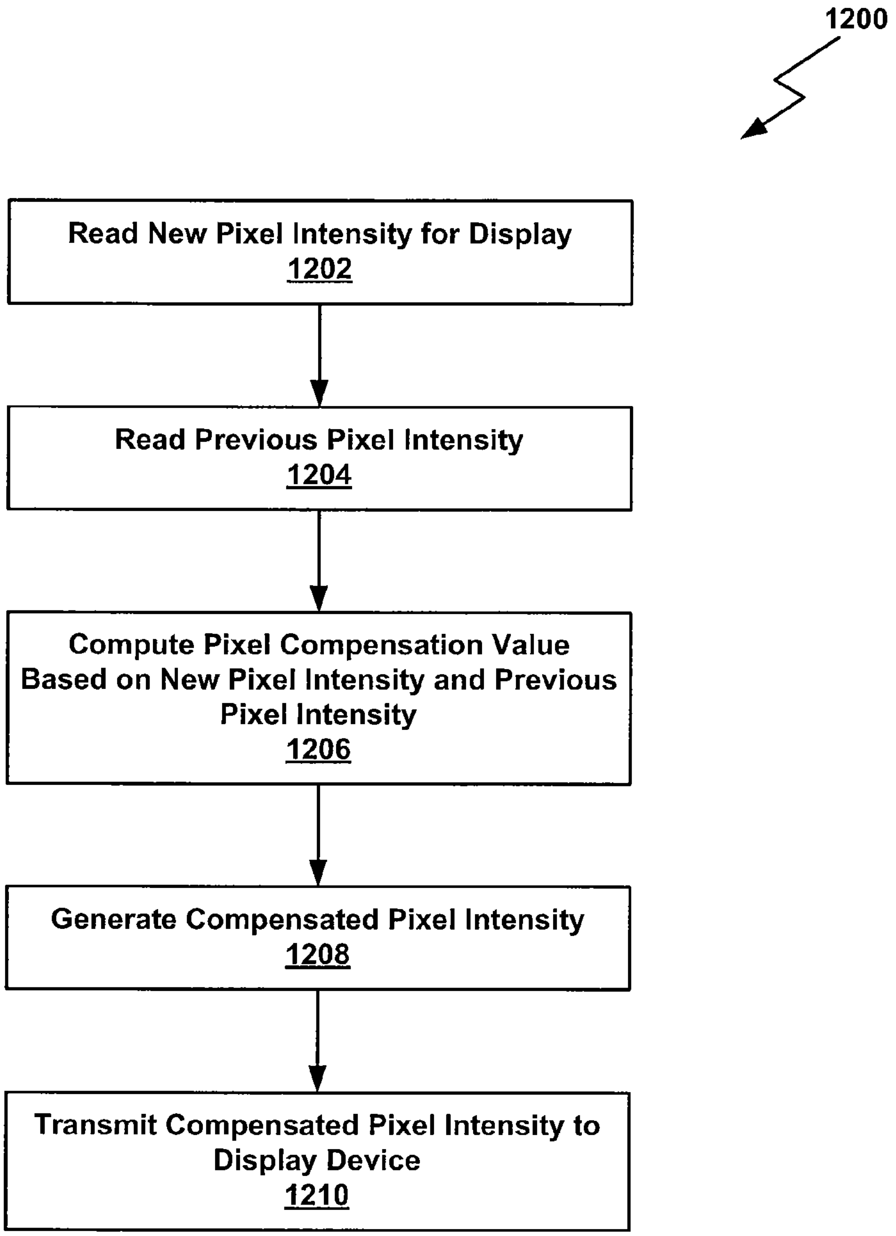
FIG. 12 is a flow diagram of method steps for computing compensated pixel intensity, according to one embodiment of the present invention.

FIG. 12 is a flow diagram of method steps 1200 for computing compensated pixel intensity, according to one embodiment of the present invention. Although the method steps are described in conjunction with the systems of FIGS. 1-7B, and 9-10, persons skilled in the art will understand that any system configured to perform the method steps, in any order, is within the scope of the invention.

The method begins in step 1202, where the scan out logic 560 reads a new pixel intensity value for display on LCD panel 520. The new pixel intensity value represents a target for actual display, and does not include compensation for a previous pixel intensity value. In one embodiment, the new pixel intensity value is read from a data structure such as a display frame or field within a display frame. In step 1204, the scan out logic 560 reads a previous pixel intensity value from a previously displayed frame of data. In step 1206, the scan out logic 560 computes a pixel compensation value based on the new pixel intensity value and previous pixel intensity value. Any technically feasible technique may be used to compute the pixel compensation value, which should account for a charging time constant and a voltage difference. In one embodiment, a lookup table is used to compute the pixel compensation value.

In step 1208, the scan out logic 560 generates a compensated pixel intensity value based on the new pixel intensity value and the pixel compensation value. In one embodiment, the new pixel intensity value is added to the pixel compensation value. The method terminates in step 1210, where the scan out logic 560 transmits the compensated pixel intensity value to the display device 110 of FIG. 1.

Persons skilled in the art will recognize that any subsystem within parallel processing subsystem 112 may be configured to perform the method steps 1200 without departing the scope and spirit of the present invention. For example, a shader program may be configured to operate on frame buffer information stored within PP memory 204 to compute compensated pixel intensity values. Alternatively, the sub-frame extraction engines 650 and 750 may be configured to compute compensated pixel intensity values by extracting sub-frame information from a current RGB packed image and a previous RGB packed image.

Figure 13:
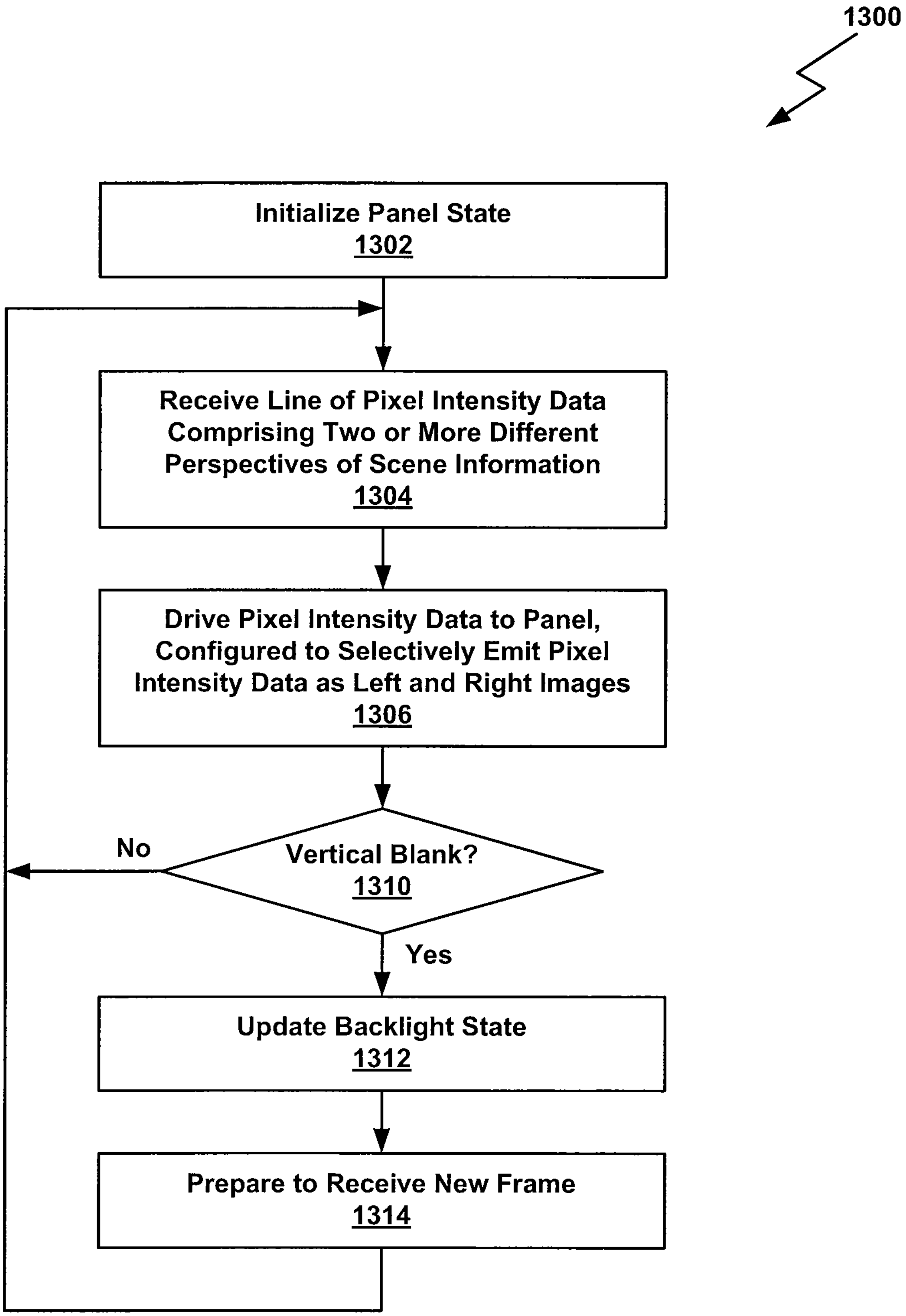
FIG. 13 is a flow diagram of method steps for computing a compensated pixel value, according to one embodiment of the present invention.

FIG. 13 is a flow diagram of method steps 1300 for displaying auto-stereoscopic images on a color field sequential display, according to one embodiment of the present invention. Although the method steps are described in conjunction with the systems of FIGS. 1-7B, and 9-10, persons skilled in the art will understand that any system configured to perform the method steps, in any order, is within the scope of the invention.

The method begins in step 1302, where panel state is initialized. In one embodiment, backlight 530 of FIG. 5A is turned off in preparation for a new frame of display data, and refresh control logic 510 is reset and configured to start receiving a new frame. In one or more embodiments involving the parallax barrier auto-stereoscopic display 1000 of FIG. 10, the parallax barrier 1010 is configured to be on (opaque).

In step 1304, refresh control logic 510 receives a line of pixel intensity data comprising two or more different perspectives of scene information. The two or more different perspectives are organized horizontally adjacent pixel locations. In one or more embodiments, parallax barrier 1010 is configured to separate the two or more different perspectives into two or more corresponding pairs of left and right images.

In one embodiment, the parallax barrier 1010 is a dynamically variable optical structure, which may be implemented using an optical LCD stack positioned to mask the display area of the LCD panel 520. The optical LCD stack comprises polarizing filters and an LCD Element that forms a pattern of opaque barrier lines. When enabled, the optical LCD stack can present opaque light barrier lines of specific orientation wherein neighboring lines are simultaneously addressable to form combined barriers of variable width. The barrier lines provide a parallax barrier that is dynamically adjustable by turning on specific neighboring lines, or arrays of addressable lines, within the optical LCD stack. Such dynamic adjustment enables moving and aligning said barrier lines with respect to underlying image pixels associated with the LCD panel 520. Moving and aligning the barrier lines advantageously enables adjustment of a view stance and viewer angle with respect to the parallax barrier auto-stereoscopic display 1000. Additionally, the barrier width may be adjusted dynamically to achieve optimal left/right eye image separation while compensating for viewer distance from the parallax barrier auto-stereoscopic display 1000.

In step 1306, the refresh control logic 510 drives the line of pixel intensity data to the LCD panel 520 via panel drivers 512. In one or more embodiments, the LCD panel 520 is configured to form color field sequential display 920 of FIG. 9. A lenticular array 910 is disposed between the color field sequential display 920 and a viewer having a left eye 950 and a right eye 952. Left image pixels, such as left image pixel 912, are optically directed to left eye 950. Similarly, right image pixels, such as right image pixel 914, are optically directed to right eye 952. Left and right image pixels are associated with a given perspective, and one or more different perspectives may be represented with corresponding unit sets of left and right image pixels.

In one or more alternative embodiments, the LCD panel 520 is configured to form color field sequential display 1020 of FIG. 10. A parallax barrier 1010 is disposed between the color field sequential display 1020 and a viewer having a left eye 1050 and a right eye 1052. Left image pixels, such as left image pixel 1012, are visible to left eye 1050. However, pixels other than left image pixels are substantially blocked from view of the left eye 1050 by the parallax barrier 1010. Similarly, right image pixels, such as right image pixel 1014, are visible to right eye 1052. Pixels other than right image pixels are substantially blocked from view of the right eye 1052. Left and right image pixels are associated with a given perspective, and one or more different perspectives may be represented with corresponding unit sets of left and right image pixels. In embodiments comprising lenticular auto-stereoscopic display 900 as well embodiments comprising parallax barrier auto-stereoscopic display 1000, the intensity data is selectively emitted as left and right images associated with a particular perspective.

If, in step 1310, a vertical blank is detected by the refresh control logic 510, then the method proceeds to step 1312. In step 1312, backlight state is updated by backlight control 514. Backlight state includes which light sources, such as LEDs 532, disposed within the backlight 530 are turned on, and with what average intensity. When a current frame of data represents a red color channel, then a red light source, such as LED 532-R, is turned on. When the current frame of data represents a green color channel, then a green light source, such as LED 532-G, is turned on, and so forth. In step 1314, the refresh control logic 510 prepares to receive a new frame of image data after a vertical blanking time. In one embodiment, the backlight is turned off in step 1314. The method then proceeds back to step 1304.

If, in step 1310, a vertical blank is not detected by the refresh control logic 510, then the method proceeds back to step 1304. The method steps 1300 are repeated over sequential frames of image data associated with different color channels of a color image. The method steps 1300 are further repeated over sequential color images comprising an arbitrary duration of video data.

In sum, a technique for generating and transmitting frame data for a color field sequential display device is disclosed. In one embodiment, separate color frames are extracted and stored from an RGB packed image. The separate color frames are transmitted to a color field sequential display device for presentation. A backlight is configured to generate an appropriate color of illumination for a currently displayed frame. In another embodiment, color fields are extracted and stored from the RGB packed image. The separate color fields reside within a single frame in memory and transmitted using a modulated pixel clock that extends vertical blank time. The backlight is configured to generate an appropriate color of illumination for a currently displayed field. A new pixel value for display may be modified to compensate for a difference between the new pixel value and a previous pixel value. The difference can lead to inter-frame noise interference that degrades image quality. Compensating the new pixel value reduces inter-frame noise. Furthermore, an auto-stereoscopic display based on the color field sequential display device is advantageous versus the prior art because chromatic fringing associated with conventional RGB display technology is eliminated in the color field sequential display device.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

The invention has been described above with reference to specific embodiments. Persons skilled in the art, however, will understand that various modifications and changes may be made thereto without departing from the broader spirit and scope of the invention as set forth in the appended claims. The foregoing description and drawings are, accordingly, to be regarded in an illustrative rather than a restrictive sense.

I claim:

1. A method for displaying color frame information on a color field sequential display, the method comprising:

reading pixel data from an input frame buffer that is organized as packed color channels, wherein a separate color channel exists for each color in the color field of the sequential display;

extracting color channel information from the pixel data for each color channel shifting and masking the pixel data for each color channel being extracted;

generating frame buffer write data from the color channel information; and storing the frame buffer write data as color sub-frame information in a target frame buffer.

2. The method of claim 1, further comprising the step of displaying the color sub-frame information stored in the target frame buffer on the color field sequential display.

3. The method of claim 1, wherein the step of generating comprises accumulating color channel information to form at least one word of write data for each color channel.

4. The method of claim 3, wherein the step of generating further comprises performing at least one color space conversion operation on the color channel information to compute the at least one word of write data.

5. The method of claim 2, wherein the color sub-frame information is organized in the target frame buffer to form a separate color sub-frame for each color channel.

6. The method of claim 5, wherein, for each independent color sub-frame, the step of displaying comprises:

directing a backlight within the color field sequential display to turn off;

transmitting contents of the independent color sub-frame to the color field sequential display; and directing the backlight within the color field sequential display to turn on a color light source corresponding to the color channel associated with the independent color sub-frame.

7. The method of claim 6, wherein the backlight is directed to turn on during a time interval that maximizes illumination time for a corresponding color sub-frame that has been written to the color field sequential display.

8. The method of claim 6, wherein, for each independent color sub-frame, the step of transmitting contents comprises:

reading current frame data from the independent color sub-frame and previous frame data for a corresponding, previously displayed independent color sub-frame;

computing compensated pixel values based on the current frame data and the previous frame data; and transmitting the compensated pixel values to the color field sequential display.

9. The method of claim 2, wherein the color sub-frame information is organized in the target frame buffer to include an independent color field for each color channel residing within a single frame.

10. The method of claim 9, wherein, for each independent color field, the step of displaying comprises:

directing a backlight within the color field sequential display to turn off;

transmitting contents of the color field to the color field sequential display based on a pixel clock operating at a first frequency;

transmitting vertical blanking lines to the color field sequential display based on the pixel clock operating at a second frequency that is less than the first frequency; and directing the backlight within the color field sequential display to turn on a color light source corresponding to the color channel associated with the independent color field.

11. The method of claim 10, wherein transmitting the contents based on the first frequency and transmitting vertical blanking lines based on the second frequency results in a specified frame refresh time.

12. The method of claim 10, wherein the backlight is directed to turn on during a time interval that maximizes illumination time for a corresponding color field that has been written to the color field sequential display.

13. The method of claim 10, wherein, for each independent color field, the step of transmitting contents comprises:

reading current field data from the independent color field and previous field data for a corresponding, previously displayed independent color field;

computing compensated pixel values based on the current field data and the previous field data; and transmitting the compensated pixel values to the color field sequential display.

14. An apparatus configured to generate color field sequential display information, comprising:

a graphics processing unit configured to:

read pixel data from an input frame buffer that is organized as packed color channels, wherein a separate color channel exists for each color in the color field of the sequential display;

extract color channel information from the pixel data for each color channel by shifting and masking the pixel data for each color channel being extracted;

generate frame buffer write data from the color channel information; and store the frame buffer write data as color sub-frame information in a target frame buffer.

15. The apparatus of claim 14, wherein the color sub-frame information is organized in the target frame buffer to include an independent color sub-frame for each color channel, and wherein the graphics processing unit is further configured to:

direct a backlight within the color field sequential display to turn off;

transmit contents of the independent color sub-frame to the color field sequential display; and direct the backlight within the color field sequential display to turn on a color light source corresponding to the color channel associated with the independent color sub-frame.

16. The apparatus of claim 15, wherein to transmit, for each independent color sub-frame, the graphics processing unit is configured to:

read current frame data from the independent color sub-frame and previous frame data for a corresponding, previously displayed independent color sub-frame;

compute compensated pixel values based on the current frame data and the previous frame data; and transmit the compensated pixel values to the color field sequential display.

17. The apparatus of claim 14, wherein the color sub-frame information is organized in the target frame buffer to include an independent color field for each color channel residing within a single frame, and wherein, for each independent color field, the graphics processing unit is further configured to:

direct a backlight within the color field sequential display to turn off;

transmit contents of the independent color field to the color field sequential display based on a pixel clock operating at a first frequency;

transmit vertical blanking lines to the color field sequential display based on the pixel clock operating at a second frequency that is less than the first frequency; and direct the backlight within the color field sequential display to turn on a color light source corresponding to the color channel associated with the independent color field.

18. The apparatus of claim 17, wherein transmitting the contents based on the first frequency and transmitting vertical blanking lines based on the second frequency results in a specified frame refresh time.

19. The apparatus of claim 17, wherein the backlight is directed to turn on during a time interval that maximizes illumination time for a corresponding color field that has been written to the color field sequential display.

20. The apparatus of claim 17, wherein to transmit contents, for each independent color field, the graphics processing unit is configured to:

read current field data from the independent color field and previous field data for a corresponding, previously displayed independent color field;

compute compensated pixel values based on the current field data and the previous field data; and transmit the compensated pixel values to the color field sequential display.

21. A computer-readable storage medium including instructions that, when executed by a processor, cause the processor to perform the steps of:

reading pixel data from an input frame buffer that is organized as packed color channels, wherein a separate color channel exists for each color in the color field of the sequential display;

extracting color channel information from the pixel data for each color channel by shifting and masking the pixel data for each color channel being extracted;

generating frame buffer write data from the color channel information; and storing the frame buffer write data as color sub-frame information in a target frame buffer.

22. The computer-readable storage medium of claim 21, wherein the color sub-frame information is organized in the target frame buffer to include an independent color sub-frame for each channel, further comprising instructions that cause the processor to perform the steps of:

directing a backlight within the color field sequential display to turn off;

transmitting contents of the independent color sub-frame to the color field sequential display; and directing the backlight within the color field sequential display to turn on a color light source corresponding to the color channel associated with the independent color sub-frame.

23. The computer-readable storage medium of claim 22, wherein, for each independent color sub-frame, the step of transmitting contents comprises:

reading current frame data from the independent color sub-frame and previous frame data for a corresponding, previously displayed independent color sub-frame;

computing compensated pixel values based on the current frame data and the previous frame data; and transmitting the compensated pixel values to the color field sequential display.

24. The computer-readable storage medium of claim 21, wherein the color sub-frame information is organized in the target frame buffer to include an independent color field for each color channel residing within a single frame, and for each independent color field, further comprising instructions that cause the processor to perform the steps of:

directing a backlight within the color field sequential display to turn off;

transmitting contents of the color field to the color field sequential display based on a pixel clock operating at a first frequency;

transmitting vertical blanking lines to the color field sequential display based on the pixel clock operating at a second frequency that is less than the first frequency; and directing the backlight within the color field sequential display to turn on a color light source corresponding to the color channel associated with the independent color field.

25. The computer-readable storage medium of claim 24, wherein, for each independent color field, the step of transmitting contents comprises:

reading current field data from the independent color field and previous field data for a corresponding, previously displayed independent color field;

computing compensated pixel values based on the current field data and the previous field data; and transmitting the compensated pixel values to the color field sequential display.

* * * * *

UNITED STATES PATENT AND TRADEMARK OFFICE

CERTIFICATE OF CORRECTION

PATENT NO. : 8,711,167 B2
APPLICATION NO. : 13/104867
DATED : April 29, 2014
INVENTOR(S) : David Wyatt It is certified that error appears in the above-identified patent and that said Letters Patent is hereby corrected as shown below:

Claims:

Column 25, Claim 1, Line 11, insert --by-- after channel

Signed and Sealed this
Twenty-ninth Day of July, 2014

Michelle K. Lee

Michelle K. Lee
*Deputy Director of the United States Patent and Trademark Office*